(12) United States Patent
Haywood et al.

(10) Patent No.: US 12,154,674 B2
(45) Date of Patent: Nov. 26, 2024

(54) INTERACTIVE VISUALIZATION OF HEALTH INFORMATION

(71) Applicant: Blue Cross and Blue Shield Association, Chicago, IL (US)

(72) Inventors: Trent Tyrone Haywood, Lewisville, TX (US); Carlos Ricardo Villarreal, Bloomington, IN (US); Theodore Andrew Lee, Bethlehem, PA (US); Jocelyn R. Wilder, Chicago, IL (US); Denise Guzzetta Schofield, Winnetka, IL (US); Ashmit Pyakurel, Westmont, IL (US); Brian Bettenhausen, Manitowish Waters, WI (US)

(73) Assignee: Blue Cross and Blue Shield Association, Chicago, IL (US)

( * ) Notice: Subject to any disclaimer, the term of this patent is extended or adjusted under 35 U.S.C. 154(b) by 0 days.

(21) Appl. No.: 17/657,297

(22) Filed: Mar. 30, 2022

(65) Prior Publication Data
US 2022/0319668 A1    Oct. 6, 2022

Related U.S. Application Data

(60) Provisional application No. 63/168,815, filed on Mar. 31, 2021.

(51) Int. Cl.
*G16H 20/60* (2018.01)
*G06F 16/29* (2019.01)

(52) U.S. Cl.
CPC ............. *G16H 20/60* (2018.01); *G06F 16/29* (2019.01)

(58) Field of Classification Search
CPC ........ G16H 20/60; G16H 40/20; G16H 50/30; G16H 50/80; G06F 16/29; G06Q 10/06; G06Q 30/0201; G06Q 50/22; G06Q 50/26
See application file for complete search history.

(56) References Cited

U.S. PATENT DOCUMENTS 5,734,709 A    3/1998   Dewitt et al.
6,307,573 B1   10/2001  Barros
(Continued)

FOREIGN PATENT DOCUMENTS

CN   304857845       10/2018
WO   WO2016067299    5/2016

OTHER PUBLICATIONS

D. Driver, A., Mehdizadeh, C., Bara-Garcia, S., Bodenreider, C., Lewis, J., & Wilson, S. (2019). Utilization of the maryland environmental justice screening tool: A bladensburg, maryland case study. International Journal of Environmental Research and Public Health, 16(3) t (Year: 2019).*

(Continued)

*Primary Examiner* — Amber A Misiaszek
(74) *Attorney, Agent, or Firm* — Neal, Gerber & Eisenberg LLP

(57) ABSTRACT

A system for providing an interactive visualization of health resources comprises one or more databases and one or more controllers. The one or more databases may be configured to store geographic data associated with block groups, including geographic coordinates, resources, and population data. The one or more controllers may be configured to (i) receive user selections for simulating the placement of at least one new resource of a given capacity and type on a geographic region-of-interest of a geographic map, and (ii) determine the predicted health outcomes on block group populations affected by the placement of the new resource as well as the predicted costs v. benefit for the new resource at the selected location. The system may be configured to provide real-time simulation results by avoiding recalculation of all of the block groups and resources within the block groups in the United States.

20 Claims, 21 Drawing Sheets

(56) References Cited

U.S. PATENT DOCUMENTS

| | | |
|---|---|---|
| 6,389,355 B1 | 5/2002 | Gibbs et al. |
| 6,879,836 B2 | 4/2005 | Nakamoto et al. |
| 7,158,878 B2 | 1/2007 | Rasmussen et al. |
| 7,207,012 B1 | 4/2007 | House et al. |
| D543,551 S | 5/2007 | Blencowe |
| D553,627 S | 10/2007 | Blencowe |
| D553,631 S | 10/2007 | Blencowe |
| D562,836 S | 2/2008 | Blencowe |
| D566,716 S | 4/2008 | Rasmussen et al. |
| D586,361 S | 2/2009 | Horowitz et al. |
| D586,362 S | 2/2009 | Horowitz et al. |
| D586,363 S | 2/2009 | Horowitz et al. |
| 7,509,579 B1 | 3/2009 | House et al. |
| D595,304 S | 6/2009 | Rasmussen et al. |
| D621,846 S | 8/2010 | Rasmussen et al. |
| D636,398 S | 4/2011 | Matas |
| 8,164,599 B1 | 4/2012 | Kadous et al. |
| D671,953 S | 12/2012 | Lee et al. |
| D671,954 S | 12/2012 | Wojcik et al. |
| D674,403 S | 1/2013 | Pearcy et al. |
| 8,761,491 B2 | 6/2014 | Chen et al. |
| D731,510 S | 6/2015 | Kiruluta et al. |
| D740,842 S | 10/2015 | Liu et al. |
| D755,195 S | 5/2016 | Meyers et al. |
| D757,053 S | 5/2016 | Nadiadi et al. |
| D765,107 S | 8/2016 | Heinrich et al. |
| D765,673 S | 9/2016 | Leabman |
| D767,599 S | 9/2016 | Le Pors et al. |
| D769,270 S | 10/2016 | Hazam et al. |
| D781,884 S | 3/2017 | Parmar et al. |
| D808,980 S | 1/2018 | Hazam et al. |
| D814,494 S | 4/2018 | Stiansen |
| D818,474 S | 5/2018 | Kato et al. |
| D845,973 S | 4/2019 | Jaycobs |
| D857,735 S | 8/2019 | Ferrante et al. |
| D861,705 S | 10/2019 | Inose et al. |
| D871,427 S | 12/2019 | Clark et al. |
| D879,819 S | 3/2020 | Bhardwaj et al. |
| 10,609,114 B1 | 3/2020 | Bicket et al. |
| 10,664,570 B1 | 5/2020 | Clark et al. |
| 10,783,686 B2 | 9/2020 | Cervelli et al. |
| D921,005 S | 6/2021 | Rowlett Leslie |
| 11,023,563 B2 | 6/2021 | Clark et al. |
| D926,209 S | 7/2021 | Wu et al. |
| D930,024 S | 9/2021 | Stein |
| D936,081 S | 9/2021 | Rubin et al. |
| 11,550,842 B2 | 1/2023 | Clark et al. |
| D1,009,926 S | 1/2024 | Zhao et al. |
| 2002/0145620 A1 | 10/2002 | Smith et al. |
| 2004/0021584 A1 | 2/2004 | Hartz et al. |
| 2004/0243299 A1 | 12/2004 | Scaer et al. |
| 2005/0034075 A1 | 2/2005 | Riegelman et al. |
| 2005/0222752 A1* | 10/2005 | Sokola .............. H04W 4/48 701/532 |
| 2006/0105775 A1 | 5/2006 | Von Kaenel et al. |
| 2007/0094045 A1* | 4/2007 | Cobbs .............. G16H 40/20 705/2 |
| 2007/0198299 A1 | 8/2007 | Puckrein |
| 2008/0040028 A1 | 2/2008 | Crump |
| 2008/0077474 A1 | 3/2008 | Dumas et al. |
| 2008/0082572 A1 | 4/2008 | Ballard et al. |
| 2008/0140718 A1 | 6/2008 | Evans et al. |
| 2008/0168396 A1 | 7/2008 | Matas et al. |
| 2008/0208443 A1 | 8/2008 | Massie et al. |
| 2009/0273613 A1 | 11/2009 | Subherwal et al. |
| 2011/0087503 A1 | 4/2011 | Desai |
| 2011/0173045 A1 | 7/2011 | Jaine |
| 2011/0271192 A1 | 11/2011 | Jones et al. |
| 2011/0271207 A1 | 11/2011 | Jones et al. |
| 2011/0289010 A1 | 11/2011 | Rankin, Jr. et al. |
| 2011/0301971 A1* | 12/2011 | Roesch .............. G16H 40/20 705/2 |
| 2013/0219334 A1 | 8/2013 | Campbell et al. |
| 2013/0339891 A1 | 12/2013 | Blumenberg et al. |
| 2013/0346873 A1 | 12/2013 | Vasudev et al. |
| 2014/0026088 A1 | 1/2014 | Monte |
| 2014/0108374 A1 | 4/2014 | Dodge et al. |
| 2014/0278306 A1 | 9/2014 | Taghavi et al. |
| 2015/0193595 A1 | 7/2015 | McNamara et al. |
| 2015/0278369 A1 | 10/2015 | Wong et al. |
| 2015/0371161 A1 | 12/2015 | Mueller et al. |
| 2015/0371421 A1 | 12/2015 | Hadfield |
| 2016/0055420 A1 | 2/2016 | Karanam et al. |
| 2016/0180386 A1 | 6/2016 | Konig |
| 2016/0203628 A1 | 7/2016 | Okumura |
| 2016/0299639 A1 | 10/2016 | Adams et al. |
| 2016/0314615 A1 | 10/2016 | Kim |
| 2016/0350507 A1 | 12/2016 | Guerin |
| 2017/0212992 A1 | 7/2017 | Pah et al. |
| 2017/0322710 A1 | 11/2017 | Cockburn et al. |
| 2017/0351833 A1* | 12/2017 | Cahan .............. G06Q 50/14 |
| 2018/0053326 A1 | 2/2018 | Ingrassia et al. |
| 2018/0233059 A1* | 8/2018 | Batteson .............. G09B 23/30 |
| 2019/0380020 A1 | 12/2019 | Pellegrini et al. |
| 2019/0392019 A1 | 12/2019 | Brannon et al. |
| 2020/0057555 A1 | 2/2020 | Walkin et al. |
| 2020/0286619 A1 | 9/2020 | Clark et al. |

OTHER PUBLICATIONS

ArcGIS, "Interactive Data Visualization for Spatial Analysis," YouTube, published Jun. 7, 2017, Retrieved from website https://www.youtube.com/watch?v=iPPGfEA2s2M, 2 pp.

Bresnick, "Using Visual Analytics, Big Data Dashboards for Healthcare Insights," Health IT Analytics, Sep. 18, 2017, 14 pp.

Melnkov, "Industrial Analytics Senso Map Overview Dashboard," Dribble, Dec. 8, 2016, 4 pp.

ArcGIS Enterprise Team, "What's new in ArcGIS Enterprise 10.6: Analysis tools," ArcGIS Blog, Jan. 18, 2018, 3 pp.

* cited by examiner

INTERACTIVE VISUALIZATION OF HEALTH INFORMATION

CROSS-REFERENCE TO RELATED APPLICATION

This application claims the benefit of U.S. Provisional Application No. 63/168,815, filed on Mar. 31, 2021, which is incorporated by reference herein in its entirety.

BACKGROUND

This disclosure relates generally to apparatuses and methods for enabling a user to visualize health-related information.

A common challenge for community planners, nutritionists, doctors and other healthcare providers, and business owners across the country is where to build new resources and to identify the type of new resources that will make the greatest impact on health-related outcomes for the population of residents who can access the new resources. For example, nutrition deserts exist in communities throughout the United States. For community leaders with limited resources to incentivize community development, it is a challenge to decide where to locate new resources that will reduce obesity and enhance community wellness, for example. Convenience stores are relatively inexpensive to build but have limited nutritional selections for consumers. By contrast, grocery stores are more expensive to build and operate as they require more employees, but they tend to have a greater number of nutritional food items for consumers.

Thus, no system or method is known to the inventors of the instant disclosure to help community planners, nutritionists, doctors and other healthcare providers, and business owners across the country to determine where to locate new resources to maximize health-related outcomes for the population of residents on community. The computational load is itself a barrier to solving this problem because modern computing methods would require days to compute any simulation of existing resources for the hundreds of thousands of communities across the United States. Moreover, prior to the instant disclosure, no system or method is known to enable the real-time simulation of the impact of new resources placed in nutritional deserts, for example on health-related outcomes for the population of residents in the community.

Consequently, there exists a need for a system and/or method that solves these and other problems.

SUMMARY

In one embodiment, a system for providing an interactive visualization of health resources is disclosed, comprising: (a) one or more databases configured to store: (i) geographic coordinates of block groups; (ii) geographic coordinates and current crowding levels of resources; and (iii) desert levels of the block groups for resource types; and (b) one or more controllers configured to: (i) generate an interface of a geographic region-of-interest for a computing device of a user, the geographic region-of-interest at least partially including one or more of the block groups; (ii) receive a selected resource type via the computing device of the user; (iii) for each block group located within the geographic region-of-interest, retrieve a respective desert level for the selected resource type; (iv) receive a user input identifying geographic coordinates of a proposed new resource for the selected resource type within the geographic region-of-interest; (v) determine, in real time, one or more affected block groups that are affected by the proposed new resource via a point-set intersection routine that determines intersecting regions of overlap between spheres of daily economic activity of respective adjacent block groups; (vi) identify, for each affected block group, a distance between the proposed new resource and a center point of the affected block group; (vii) identify one or more affected resources that are affected by the proposed new resource; (viii) determine, in real time, a new crowding level of each affected resource, wherein the current crowding level of each affected resource is concatenated together with a new crowding level for the proposed new resource; (ix) determine, in real time, a new desert score of each affected block group located within the geographic region-of-interest of the interface based on the new crowding level of each affected resource; and (x) update, in real time, the interface to display the new desert score of each affected block group located within the geographic region-of-interest.

For each block group and prior to receipt of the user input, the one or more controllers may be configured to: (i) determine an average estimated distance traveled by residents of the block group; (ii) identify a geographic population distribution of the residents within the block group; (iii) determine a population-weighted spatial center of the block group, the center point of the block group being the population-weighted spatial center; (iv) determine the sphere of daily economic activity of the block group based on the population-weighted spatial center and the average estimated distance; and (v) store geographic coordinates of the population-weighted spatial center and the average estimated distance in the one or more databases.

For each block group and prior to the receipt of the user input, the one or more controllers may be configured to identify which of the resources are located within the sphere of daily economic activity of the block group, and for each resource located within the sphere of daily economic activity: (i) determine the distance between the resource and the population-weighted spatial center of the block group; and (ii) store the distance in the one or more databases.

For each combination of one of the block groups and one of the resources located within a corresponding sphere of daily economic activity, the one or more controllers may be configured to calculate, based on proximity, a percentage of residents predicted to travel to the resource. To calculate the percentage of residents predicted to travel to the resource, the one or more controllers may be configured to apply a cubic delay function to the distance between the center point of the block group and the resource.

For each resource of each resource type located within a respective sphere of daily economic activity of one or more of the block groups, the one or more controllers is configured to: (i) identify a capacity level of the resource; and (ii) determine the current crowding level for the resource based on the capacity level and a number of residents predicted to travel to the resource.

For each combination of one of the block groups and one of the resource types, the one or more controllers may be configured to determine a respective one of the desert levels based on each current crowding level of a respective one or more of the resources located within a sphere of daily economic activity of the one of the block groups.

In another embodiment, a method for providing an interactive visualization of health resources is disclosed, comprising: (i) storing, via one or more databases, geographic coordinates of block groups, geographic coordinates and current crowding levels of resources, and desert levels of the block groups for resource types; (ii) generating, via one or more controllers, an interface of a geographic region-of-interest for a computing device of a user, the geographic region-of-interest at least partially including one or more of the block groups; (iii) receiving a selected resource type via the computing device of the user; (iv) for each block group located within the geographic region-of-interest, retrieving a respective desert level for the selected resource type; (v) receiving, via the computing device of the user, a user input that identifies geographic coordinates of a proposed new resource for the selected resource type within the geographic region-of-interest; (vi) determining, in real time, one or more affected block groups that are affected by the proposed new resource via a point-set intersection routine that determines intersecting regions of overlap between spheres of daily economic activity of respective adjacent block groups; (vii) identifying, for each affected block group, a distance between the proposed new resource and a center point of the affected block group; (viii) identifying one or more affected resources that are affected by the proposed new resource; (ix) determining, in real time, a new crowding level of each affected resource, wherein the current crowding level of each affected resource is concatenated together with a new crowding level for the proposed new resource; (x) determining, in real time, a new desert score of each affected block group located within the geographic region-of-interest of the interface based on the new crowding level of each affected resource; and (xi) updating, in real time, the interface to display the user input and the new desert score of each affected block group located within the geographic region-of-interest.

For each of the block groups and prior to receipt of the user input, the method may include: (i) determining an average estimated distance traveled by residents of the block group; (ii) identifying a geographic population distribution of the residents within the block group; (iii) determining a population-weighted spatial center of the block group, the center point of the block group being the population-weighted spatial center; (iv) determining the sphere of daily economic activity of the block group based on the population-weighted spatial center and the average estimated distance; and (iv) storing geographic coordinates of the population-weighted spatial center and the average estimated distance in the one or more databases.

For each of the block groups and prior to the receipt of the user input, the method may include: identifying which of the resources are located within the sphere of daily economic activity of the block group, and for each resource located within the sphere of daily economic activity: (i) determining the distance between the resource and the population-weighted spatial center of the block group; and (ii) storing the distance in the one or more databases.

For each combination of one of the block groups and one of the resources located within a corresponding sphere of daily economic activity, the method may include calculating, based on proximity, a percentage of residents predicted to travel to the resource. The step of calculating the percentage of residents predicted to travel to the resource may include applying a cubic delay function to the distance between the center point of the block group and the resource.

For each resource of each resource type located within a respective sphere of daily economic activity of one or more of the block groups, the method may include: (i) identifying a capacity level of the resource; and (ii) determining the current crowding level for the resource based on the capacity level and a number of residents predicted to travel to the resource.

For each combination of one of the block groups and one of the resource types, the method may include determining a respective one of the desert levels based on each current crowding level of a respective one or more of the resources located within a sphere of daily economic activity of the one of the block groups.

In another embodiment, a computer readable medium comprising instructions, which, when executed by a processor, causes a machine to: (i) store geographic coordinates of block groups, geographic coordinates and current crowding levels of resources, and desert levels of the block groups for resource types; (ii) generate an interface of a geographic region-of-interest for a computing device of a user, the geographic region-of-interest at least partially including one or more of the block groups; (iii) receive a selected resource type via the computing device of the user; (iv) for each block group located within the geographic region-of-interest, retrieve a respective desert level for the selected resource type; (v) receive, via the computing device of the user, a user input that identifies geographic coordinates of a proposed new resource for the selected resource type within the geographic region-of-interest; (vi) determine, in real time, one or more affected block groups that are affected by the proposed new resource; (vii) identify, for each affected block group, a distance between the proposed new resource and a center point of the affected block group; (viii) identify one or more affected resources that are affected by the proposed new resource; (ix) determine, in real time, a new crowding level of each affected resource, wherein the current crowding level of each affected resource is concatenated together with a new crowding level for the proposed new resource; (x) determine, in real time, a new desert score of each affected block group located within the geographic region-of-interest of the interface based on the new crowding level of each affected resource; and (xi) update, in real time, the interface to display the user input and the new desert score of each affected block group located within the geographic region-of-interest.

For each of the block groups and prior to receipt of the user input, the instructions, when executed by the processor, the machine may be configured to: (i) determine an average estimated distance traveled by residents of the block group; (ii) identify a geographic population distribution of the residents within the block group; (iii) determine a population-weighted spatial center of the block group, the center point of the block group being the population-weighted spatial center; (iv) determine the sphere of daily economic activity of the block group based on the population-weighted spatial center and the average estimated distance; and (v) store geographic coordinates of the population-weighted spatial center and the average estimated distance in the one or more databases.

For each of the block groups and prior to the receipt of the user input, the instructions, when executed by the processor, the machine may be configured to: (i) identify which of the resources are located within the sphere of daily economic activity of the block group; and (ii) for each resource located within the sphere of daily economic activity, determine the distance between the resource and the population-weighted spatial center of the block group.

For each combination of one of the block groups and one of the resources located within a corresponding sphere of daily economic activity, the instructions, when executed by the processor, may cause the machine to calculate, based on proximity, a percentage of residents predicted to travel to the resource by applying a cubic delay function to the distance between the center point of the block group and the resource.

For each resource of each resource type located within a respective sphere of daily economic activity of one or more of the block groups, the instructions, when executed by the processor, may cause the machine to identify a capacity level of the resource and determine the current crowding level for the resource based on the capacity level and a number of residents predicted to travel to the resource.

For each combination of one of the block groups and one of the resource types, the instructions, when executed by the processor, may cause the machine to determine a respective one of the desert levels based on each current crowding level of a respective one or more of the resources located within a sphere of daily economic activity of the one of the block groups.

BRIEF DESCRIPTION OF THE DRAWINGS

The file of this patent application contains at least one drawing executed in color. Copies of this patent application with color drawing(s) will be provided by the Office upon request and payment of the necessary fee.

For a better understanding of the features described in this disclosure, reference may be made to embodiments shown in the drawings. The components in the drawings are not necessarily to scale, and related elements may be omitted so as to emphasize and clearly illustrate the novel features described herein. In addition, system components can be variously arranged, as known in the art. In the figures, like referenced numerals may refer to like parts throughout the different figures unless otherwise specified.

DETAILED DESCRIPTION

Figure 1:
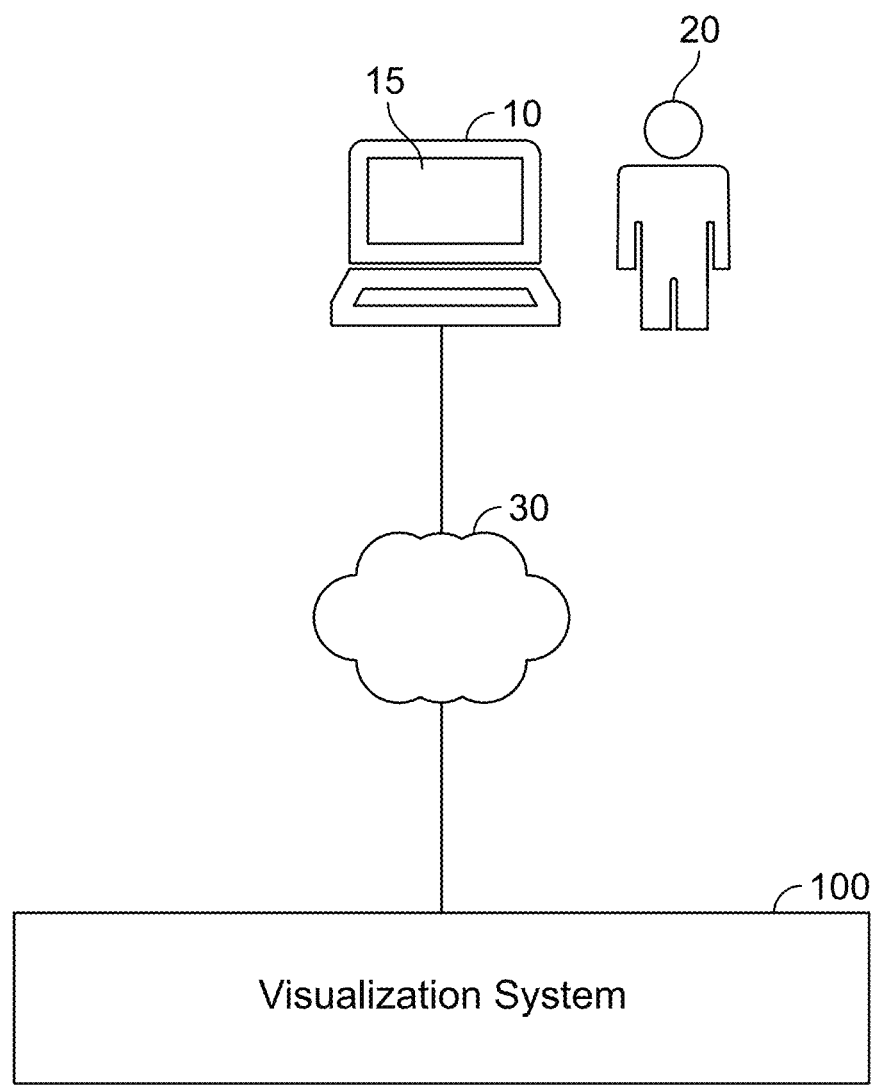
FIG. 1 depicts an example environment according to the instant disclosure in which a visualization system generates an interactive visualization of health information.

While the features, methods, devices, and systems described herein may be embodied in various forms, there are shown in the drawings, and will hereinafter be described, some exemplary and non-limiting embodiments. Not all of the depicted components described in this disclosure may be required, however, and some implementations may include additional, different, or fewer components from those expressly described in this disclosure. Variations in the arrangement and type of the components may be made without departing from the spirit or scope of the claims as set forth herein.

The instant disclosure describes and illustrates various embodiments of a health information visualization system and method for using same. The visualization system includes hardware and software for carrying out a dynamic, real-time, interactive user experience that enables the user to visualize, via the user's remote display, the impact of notionally locating a new, health-related resource on a geographical map. The impact can be characterized by a number of different metrics, including (1) utilization and demographic metrics for people residing in proximity to the new resource and corresponding reduction in utilization of pre-existing geographically proximate resources, and (2) improved health outcomes for people residing near the new resource.

Pre-existing health-related resources across the United States may be known or derived from publicly available sources. Likewise, the physical geographical location, by latitude and longitude or other geographic locator, of all such health-related resources may also be known from publicly available sources. In various embodiments, pre-existing health-related resources and their physical geographical location may be taken from or derived from data derived from publicly available sources such as local health departments, privately held data such as data available from the Blue Cross and Blue Shield® Provider Data Repository, or purchased from vendors such as Infogroup. In various embodiments, the health-related resources may include: (1) primary care physicians and any other medical service professionals including physical therapy practitioners, chiropractic practitioners, massage therapists, counselors/psychologists/psychiatrists, dentists, podiatrists, optometrists, and the like; (2) locations for health or medical-related treatments including the offices of the medical service professionals noted above, urgent care centers, clinics, hospitals and trauma centers, medication assisted treatment centers, diagnostic imaging offices, fitness centers and gyms, and the like; and (3) sources of nutrition such as grocery stores, convenience stores, drug stores and pharmacies where food items are sold, gas stations where food items are sold, large box stores, restaurants, coffee shops, and the like. Health-related resources can be any medical (mental or physical) and/or nutrition-related resource.

The system of the instant disclosure enables a user to obtain the real-time effect of positioning a new health-related resource anywhere on a displayed map. In various embodiments, the system of the instant disclosure may be configured to (1) receive a user's geographical selection on a map displayed on the user's computer display and interpret the selected location on the displayed map as being the location of a desired location for the placement of a new resource, (2) rapidly, in real-time, compute the effect of the new resource on communities near the newly located resource to, for example, predict health outcomes on people and health-related cost savings in the affected communities, and (3) display, in real-time, the computed effect of the newly located resource on the user's computer display. In various embodiments, the system may be configured to receive the users instruction using different digitizing tools, including a computer mouse, digitizer pen, trackpad, or other input device such as a touchscreen. For purposes of the instant disclosure, the term "pin drop" may be used to describe the foregoing steps 1 through 3 or parts thereof.

In various embodiments, the system can be configured to take into account the local movement patterns of people in a community or region to develop a measure of resource scarcity for the community or region. Movements of people in the community or region may be characterized by various modes of human travel including automobile, bus, subway, commuter rail, walking, cabs, and bicycles, and the like. Each mode of transportation may be associated with an average distance traveled and an average travel time by people in each community or region. In various embodiments, the system may utilize de-identified, publicly distributed, neighborhood aggregate responses to questions 32-35 of the American Community Survey, which detail the number of commuters by travel mode, further partitioned by travel time within each travel mode category. For example, the estimated distance traveled for each travel mode within each travel time band arises from the following national average travel speeds by travel mode:

| 1. | Car: | 30 mph |
| 2. | Bus: | 5 mph |
| 3. | Subway: | 15 mph |
| 4. | Commuter Rail: | 30 mph |
| 5. | Walking: | 4 mph |
| 6. | Cab: | 10 mph |

The system may also utilize a measure that is designed to capture the average distance people from each community travel on a daily basis. For purposes of the instant disclosure, the term "edist" is defined as the average distance traveled among commuters in a community, and takes into account common modes of transportation in each community. The system may take into account that people from some communities, such as those in the countryside, may travel vast distances daily to reach their respective healthcare providers or to obtain groceries, while people in other communities, such as those in a city center, may travel relatively short distances daily. The system may utilize edists or any similar measure to identify the health-supporting resources that a community of people are more likely to interact with than other resources. The system may enable a user to identify each community's desert conditions reflecting the scarcity of health-supporting resources, and particularly, to identify the impact on the community's desert conditions and health outcomes of placing a new health-supporting resource on the map. The system of the instant disclosure may quantify the impact by computing and making available to the user a "desert score" for each community.

For purposes of the instant disclosure, a "block group" is a contiguous geographical area in which a community of people reside. One example of a block group is a geographical unit used by the U.S. Census Bureau called a Block Group that lies between the Census Tract and the Census Block as defined by the U.S. Census Bureau. In this example, block groups are divisions of census tracts, generally include between 600 and 3000 people, and do not cross state, county or census tract boundaries but may cross the boundaries of any other geographic entity. The system of the instant disclosure may utilize block groups, including Block Groups that are used and defined by the U.S. Census Bureau, to define the geographic latitudinal and longitudinal boundaries of each community across the United States. The boundaries of each block group may represent each community and may be represented by any number of different polygonal shapes in much the same way as zip codes have different polygonal shapes. The system may additionally utilize the population-weighted latitudinal and longitudinal center of each block group to define the center of a circle defined by a radius equal to the edist for each block group. In this way, each edist may individually represent the average distance people from each block group travel on a daily basis in every direction emanating from the population-weighted center of each block group under the assumption, for simplifying calculations, that all of the people in each block group initiate their daily journey from the population-weighted center of each block group. In various embodiments, each of the edists help define the economic sphere of daily activity of members (i.e., people) of each block group, which naturally may vary from one block group to the next, as may be derived from data from the American Community Survey. And by using a population-weighted center of each block group, the system of the instant disclosure may take into account that some block groups may have large expanses of unsettled regions including lakes, national parks, and rail yards that may make impractical any use of the geospatial center or centroid of each block group.

One of ordinary skill would appreciate that the edists may define circles that overlap circles defined by adjacent block groups, particularly in geographic regions of the United States with relatively high populations compared to regions with relatively low populations. For example, densely populated cities like Chicago, IL have less populated suburbs adjacent to the city, and even less populated country spaces that lie past the suburbs. Thus, the edists that define circles defining the economic sphere of daily activity of block groups in the city of Chicago will tend to overlap adjacent circles from adjacent block groups. By contrast, the edists that define circles defining the economic sphere of daily activity of block groups in the countryside in the State of Illinois will tend not to overlap those of adjacent blocks, or at least not to the same extent.

In addition, one of ordinary skill would appreciate that the radial length of each edist, and thus the area circumscribed by each circle, which is equivalent to the economic sphere of daily activity for each block group, may vary according to the average distance traveled by people in each respective block group. For example, people residing in the city of Chicago may have multiple modes of transportation available to them, including automobile, bus, rail, and walking, to name a few. Thus, the radial length of each edist for people residing in block groups located in the city of Chicago may be relatively short because people may not need to commute very far to reach their places of employment or their economic resources. By contrast, people residing in the far outskirts of the city of Chicago may only have a single, prominent or practical mode of transportation—the automobile. Thus, the radial length of each edist for people residing in block groups in the far outskirts of the city of Chicago may be relatively long because people in the far outskirts may naturally need to drive a greater distance than their city dwelling counterparts to reach their places of employment or their economic resources.

One of ordinary skill would additionally appreciate that cities may tend to have more employment options and other resources for residents as compared to geographical locations far away from cities. Thus, the density of resources within a particular sphere of economic activity may be higher in cities than in the countryside. That said, within various pockets of cities there may exist relative scarcity of resources compared to other pockets of cities. The system of the instant disclosure may be configured to determine for any region or location in the United States the relative scarcity of resources, which may be called "resource deserts," to a level of usable granularity. From there, the system of the instant disclosure may be configured to enable a user to determine the impact of placing additional resources in the resource deserts. That impact may include a determination of health-related outcomes that may enable users of the system of the instant disclosure to maximize the beneficial impact to people located in resource deserts, especially when there is limited availability of additional resources. The system of the instant disclosure may also enable users to easily and quickly decide which type of resource would increase health-related outcomes at the lowest cost. For example, a user may quickly determine that the addition of a retail grocery store in a particular resource desert of one or more block groups may yield higher health-related outcomes than adding, for example, a hospital to that resource desert. In addition, a user may also quickly be able to optimize the specific geographic location within the resource desert to ensure the maximum number of residents can benefit from the new resource(s).

With the economic sphere of daily activity defined for each block group (i.e., defined by a circle having a radius equal to each edist, where each edist originates at the population-weighted center of each block group) across the United States, and knowing the number, type, and latitude/longitude location of every resource that are accessible to people residing in each block group, then the system of the instant disclosure may determine a measure of resource prevalence, scarcity, or abundance for people in each block group.

As one of ordinary skill would appreciate, computing a snapshot at a given moment in time of the resource prevalence, scarcity, or abundance for each block group across the United States is incredibly time consuming and expensive in terms of computing resources, such as computer memory. There are approximately 220,000 block groups in the United States and 130,000 grocery stores, for example. To calculate the national nutritional scarcity (or alternatively, nutritional abundance) for each and every block group in the United States, the system of the instant disclosure must spatially join each block group and grocery store, resulting in 220,000×130,000 combinations. Using current computing technology, it takes the system of the instant disclosure approximately 48 hours to compute that snapshot. Datasets for other health-related resources, such as fitness centers, hospitals, etc., may range from about 30,000 to about 150,000 units nationwide, all of which only exacerbates the incredibly time consuming process for computing resource prevalence, scarcity, or abundance. In various embodiments, the resource prevalence, scarcity, or abundance for each community or block group is computed by the system of the instant disclosure and made available and/or displayed to the user as a "desert score."

Thus, to determine the impact of placing just one additional resource of a specific type within the economic sphere of daily activity for a given block group would ordinarily require waiting for another 48 hours for the solution to be computed. The system of the instant disclosure provides a novel solution to this dilemma, and enables dynamic, real-time receipt and recognition by the system of a user's selected locations for new resources as well as real-time convergence on a mathematical solution representing the impact of the new resources on the block groups affected by the placement of the new resources. The system of the instant disclosure can be configured to deliver that impact to the user in the form of data displayed in real-time on the user's remote computer display, with or without graphical visualization on a geographical map.

In short, the system of the instant disclosure solves the technical problem of exceedingly long and impractical computer processor execution times by enabling the calculation, in real-time of new block group desert scores after a user adds one or more new resources to a map, and by enabling, in real-time, the display to the user of the newly computed block group desert scores. The system of the instant disclosure provides an unconventional technological solution by including a specific set of rules to predict, in real-time, community population health-outcomes resulting from the user's selection of the type and location of new health-related resources in one or more geographical regions of the United States. The system of the instant disclosure enables rapid "what-if" assessments of isolated segments of the United States, allowing the user to choose from different types and locations for placing new resources in the isolated segments. The zoom level of the geographical map on the user's display may be dynamically chosen by the user and may vary from a nationwide view of the United States to a single community or block group. In addition, data, tabular information, boundary delineations, points or information of interest, and/or color or other visual differentiators may overlay the geographical map on the user's display.

An example system disclosed herein performs the steps of: (1) performing a baseline desert score for all of the block groups across the nation, (2) receiving user requests for new resources, (3) calculating a new desert score in real-time, and (3) providing the new desert score to the user. By doing so, the example system herein addresses the problem of exceedingly long and impractical computer processor execution times. Thus, the example disclosed herein includes a specific set of rules that provide an unconventional technological solution of enabling the calculation of new desert scores in real time to address the technological problem of exceedingly long processor execution times.

The system of the instant disclosure may leverage a community health management software platform for enabling, for example, dynamic display zoom level of geographic maps, and for providing a framework for visualizing output data from the system of the instant disclosure to the user. One such software platform is the CHM Hub® available at https://insights.chmhub.com by Blue Cross Blue Shield Institute, Inc. U.S. Pat. No. 10,664,570, the contents of which are incorporated by reference herein in their entirety, describes various aspects of the CHM Hub® software platform.

Turning now to the figures, there are shown various aspects of a visualization system 100 for carrying out the solution disclosed herein. FIG. 1, for example, shows an exemplary visualization system 100 for generating and transmitting an interactive visualization of health information over the Internet 30 to a remote user 20 using a remote computer 10 having display 15. In this embodiment, visualization system 100 may interactively communicate with user 20 by receiving instructions over the Internet 30 and by providing real-time information to user 20 for display on the remote computer 10. The information from visualization system 100 may be configured for viewing in a web browser displayed in the display 15.

In various embodiments, remote computer 10 may be any computing device, including a desktop computer, a mobile computer, a handheld computer, such as a smartphone. In various embodiments, visualization system 100 may communicate with remote computer 10 via the Internet, the world wide web, or any other communications protocol using any wired or wireless means known to one of ordinary skill, including Bluetooth, near-field communications, Wi-Fi, cellular, and/or satellite.

Figure 2:
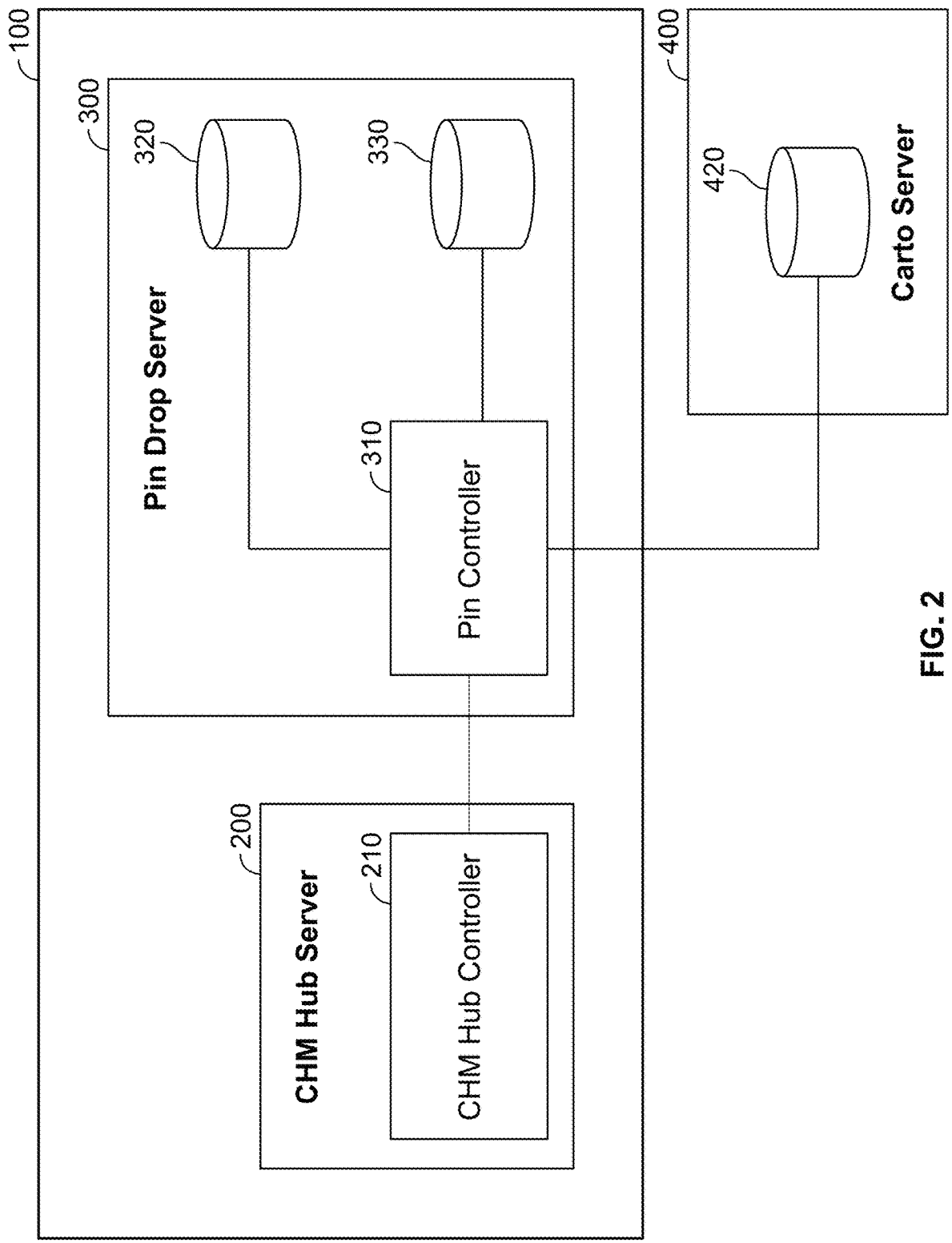
FIG. 2 further depicts the visualization system illustrated in FIG. 1.

FIG. 2 depicts various aspects of an example visualization system 100, including CHM hub server 200 comprising (1) a CHM hub controller 210, and (2) a pin drop server 300 comprising a pin drop controller 310 (also referred to as a pin controller 310), a PostgreSQL database 320, and a SQLite database 330. As shown in the illustrated example, one or more electronic components of a Carto server 400, which may include Carto database 420, may be included in or in communication with the visualization system 100.

Figure 3:
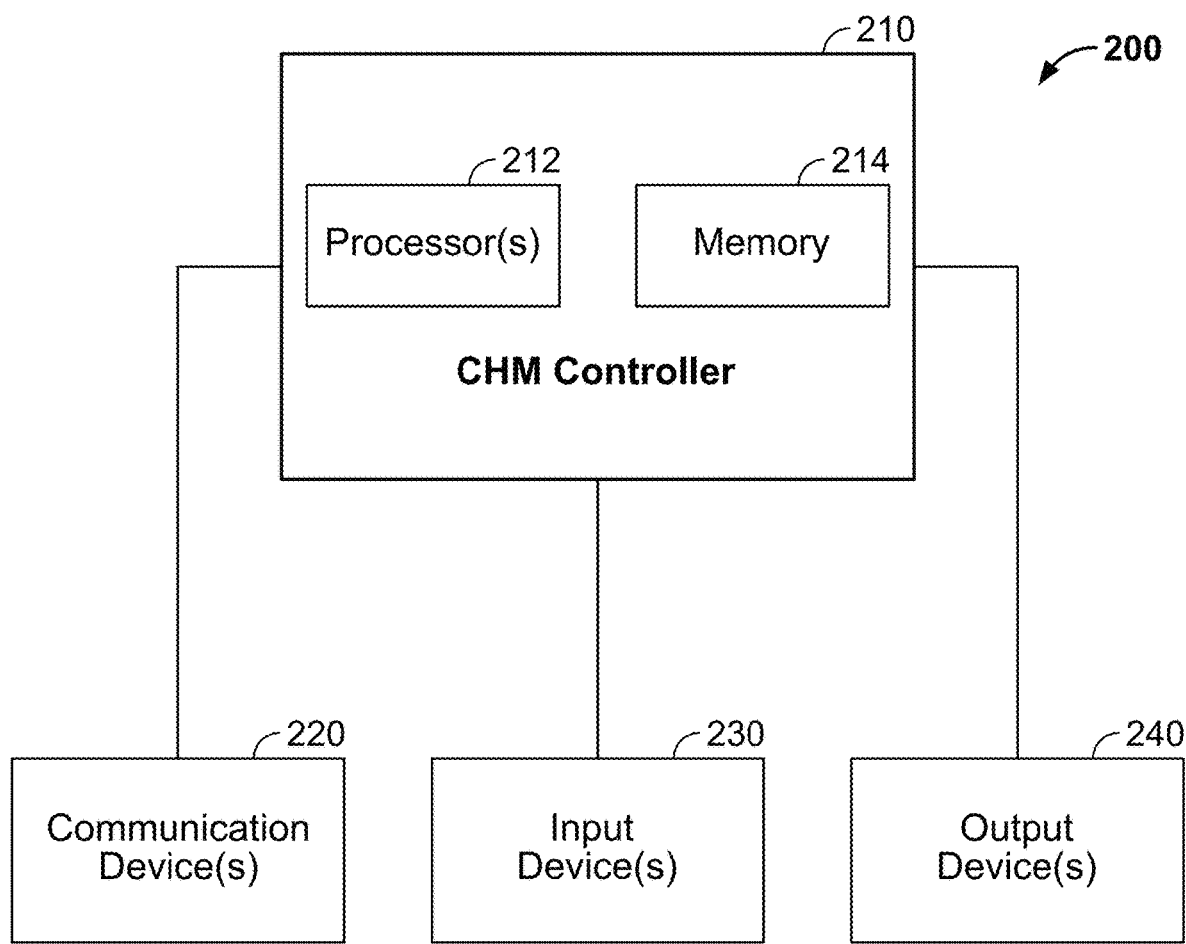
FIG. 3 is a block diagram of electronic components of a CHM hub server of the visualization system of FIG. 1.

FIG. 3 depicts electronic components of a CHM hub server 200 of an example visualization system 100. In the illustrated example, the CHM hub server 200 includes the CHM hub controller 210, one or more communication devices 220, one or more input devices 230, and one or more output devices 240.

The CHM hub controller 210 includes one or more processors 212 and memory 214. In the illustrated example, the processor(s) 212 includes any suitable processing device or set of processing devices such as, but not limited to, a microprocessor, a microcontroller-based platform, an integrated circuit, one or more field programmable gate arrays (FPGAs), and/or one or more application-specific integrated circuits (ASICs).

The memory 214 includes volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc.), and/or combinations thereof. The memory 214 is computer readable media on which one or more sets of instructions, such as the software for operating the methods of the present disclosure, can be embedded. For example, the instructions may embody one or more of the methods or logic as described herein.

The terms "non-transitory computer-readable medium" and "computer-readable medium" include a single medium or multiple media, such as a centralized or distributed database, and/or associated caches and servers that store one or more sets of instructions. Further, the terms "non-transitory computer-readable medium" and "computer-readable medium" include any tangible medium that is capable of storing, encoding or carrying a set of instructions for execution by a processor or that cause a system to perform any one or more of the methods or operations disclosed herein. As used herein, the term "computer readable medium" is expressly defined to include any type of computer readable storage device and/or storage disk and to exclude propagating signals.

The communication device(s) 220 include hardware (e.g., processor(s), memory, storage, antenna(s), etc.), software, and wired and/or wireless network interface(s) to enable communication with other server(s) (e.g., the pin drop server 300), device(s) and/or network(s) to control the wired or wireless network interfaces. Example external network(s) include a public network, such as the Internet; a private network, such as an intranet; or combinations thereof, and utilize one or more networking protocol(s) for communication.

The input device(s) 230 of the illustrated example enable an operator, such as a programmer for the CHM hub server 200, to provide instructions, commands, and/or data to the CHM hub controller 210. Examples of the input device(s) 230 include one or more of a button, a control knob, an instrument panel, a touch screen, a touchpad, a keyboard, a mouse, a speech recognition system, etc.

The output device(s) 240 of the illustrated example display output information and/or data of the CHM hub controller 210 to an operator, such as a programmer for the CHM hub server 200. Examples of the output device(s) 240 include a display (e.g., a liquid crystal display (LCD), an organic light emitting diode (OLED) display, a flat panel display, etc.) and/or any other device that visually presents information to an operator. Additionally or alternatively, the output device(s) 240 may include one or more speakers and/or any other device(s) that provide audio signals for an operator. Further, the output device(s) 240 may provide other types of output information, such as haptic signals.

Figure 4:
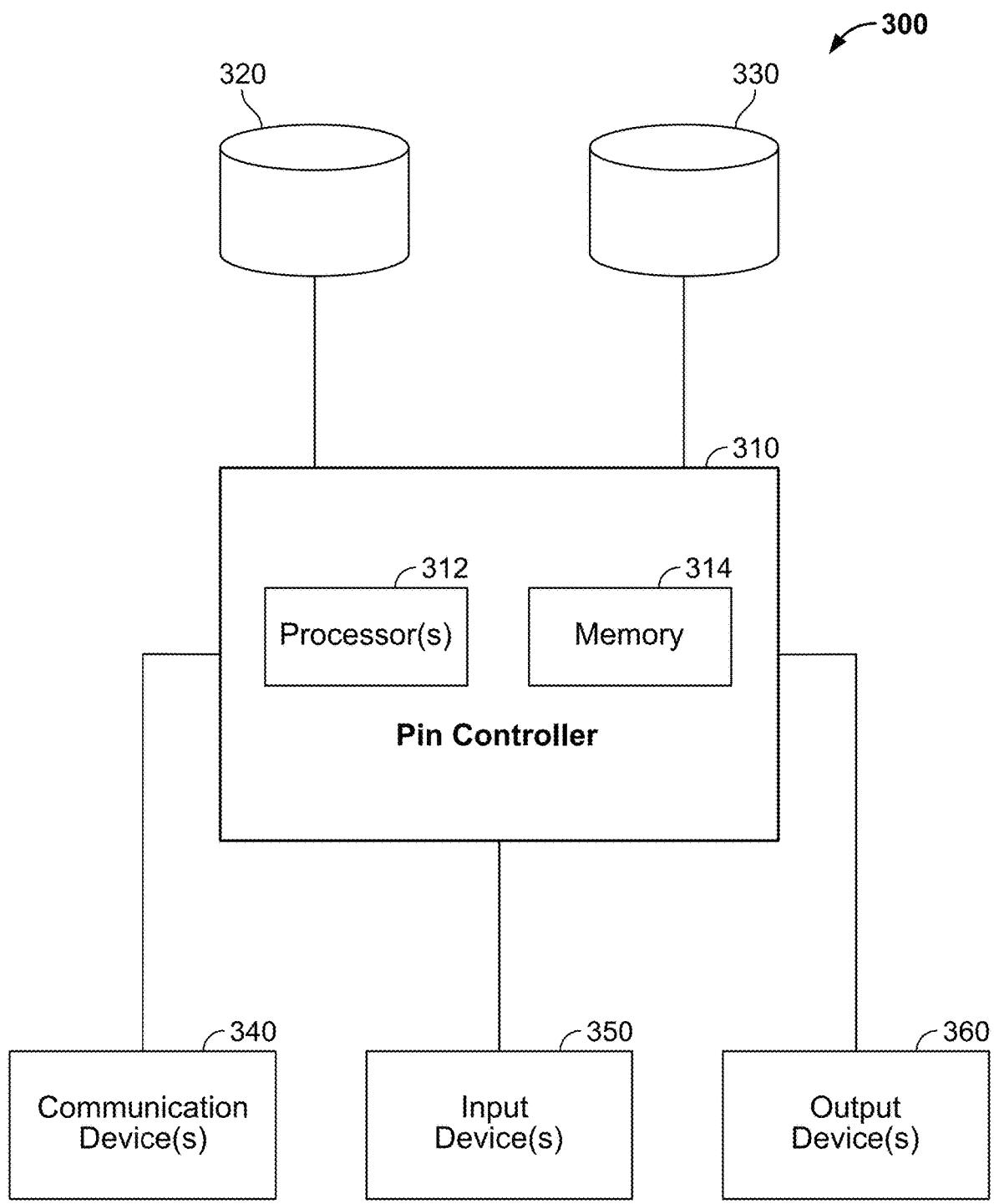
FIG. 4 is a block diagram of electronic components of a pin drop server of the visualization system of FIG. 1.

FIG. 4 depicts electronic components of a pin drop server 300 of the visualization system 100. In the illustrated example, the pin drop server 300 includes the pin drop controller 310, the PostgreSQL database 320, the SQLite database 330, one or more communication devices 340, one or more input devices 350, and one or more output devices 360.

The pin drop controller 310 includes one or more processors 312 and memory 314. In the illustrated example, the processor(s) 312 includes any suitable processing device or set of processing devices such as, but not limited to, a microprocessor, a microcontroller-based platform, an integrated circuit, one or more field programmable gate arrays (FPGAs), and/or one or more application-specific integrated circuits (ASICs).

The memory 314 includes volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc.), and/or combinations thereof. The memory 314 is computer readable media on which one or more sets of instructions, such as the software for operating the methods of the present disclosure, can be embedded. For example, the instructions may embody one or more of the methods or logic as described herein.

The communication device(s) 340 include hardware (e.g., processor(s), memory, storage, antenna(s), etc.), software, and wired and/or wireless network interface(s) to enable communication with other server(s) (e.g., the CHM hub server 200 and the Carto server 400), device(s) and/or network(s) to control the wired or wireless network interfaces. Example external network(s) include a public network, such as the Internet; a private network, such as an intranet; or combinations thereof, and utilize one or more networking protocol(s) for communication.

The input device(s) 350 of the illustrated example enable an operator, such as a programmer for the pin drop server 300, to provide instructions, commands, and/or data to the pin drop controller 310. Examples of the input device(s) 350 include one or more of a button, a control knob, an instrument panel, a touch screen, a touchpad, a keyboard, a mouse, a speech recognition system, etc.

The output device(s) 360 of the illustrated example display output information and/or data of the pin drop controller 310 to an operator, such as a programmer for the pin drop server 300. Examples of the output device(s) 360 include a display (e.g., a liquid crystal display (LCD), an organic light emitting diode (OLED) display, a flat panel display, etc.) and/or any other device that visually presents information to an operator. Additionally or alternatively, the output device(s) 360 may include one or more speakers and/or any other device(s) that provide audio signals for an operator. Further, the output device(s) 360 may provide other types of output information, such as haptic signals.

Figure 5:
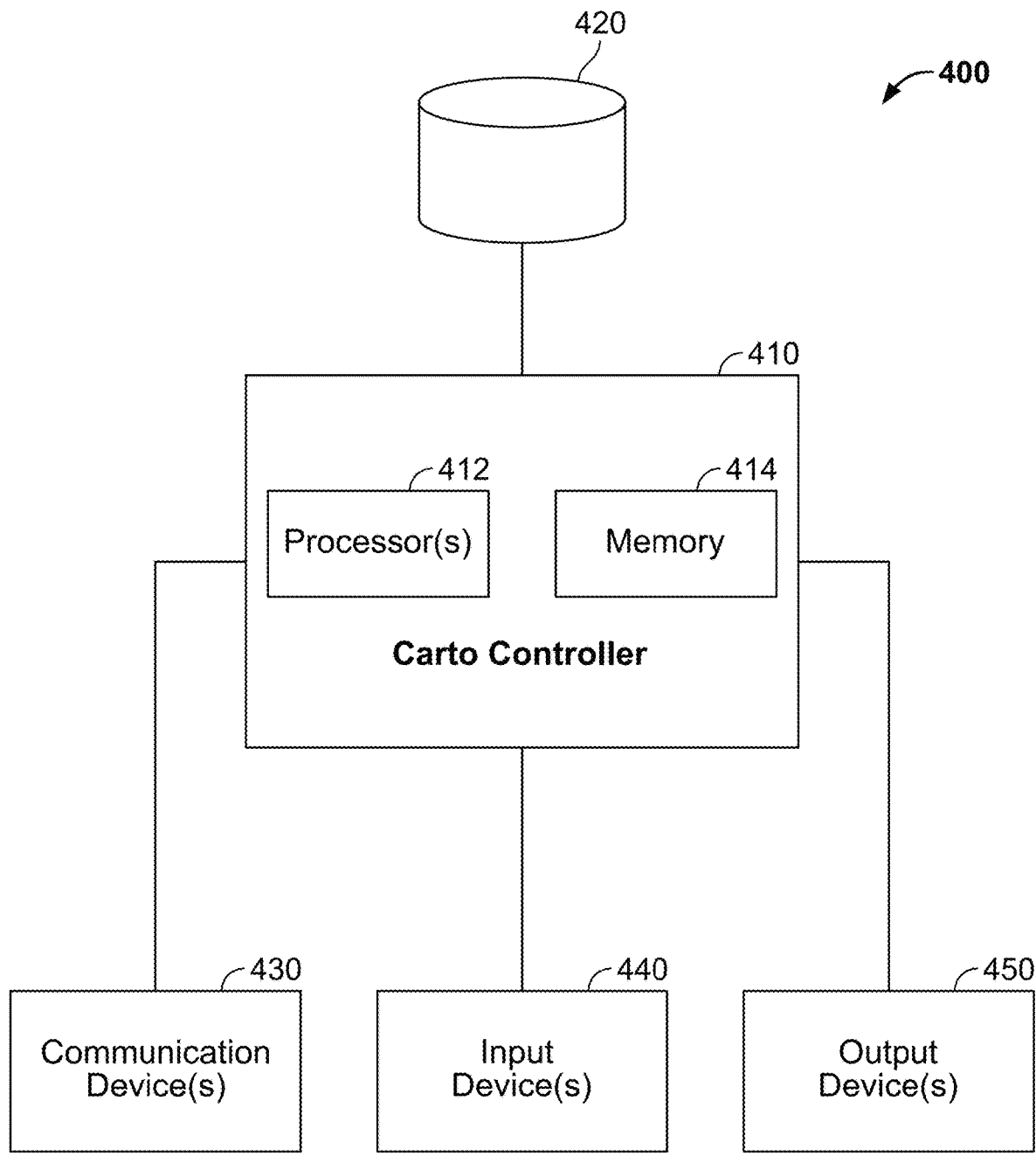
FIG. 5 is a block diagram of electronic components of a Carto server of the visualization system of FIG. 1.

FIG. 5 depicts electronic components of a Carto server 400, which may be included in or in communication with the visualization system 100. In the illustrated example, the Carto server 400 includes a Carto controller 410, the Carto database 420, one or more communication devices 430, one or more input devices 440, and one or more output devices 450.

The Carto controller 410 includes one or more processors 412 and memory 414. In the illustrated example, the processor(s) 412 includes any suitable processing device or set of processing devices such as, but not limited to, a microprocessor, a microcontroller-based platform, an integrated circuit, one or more field programmable gate arrays (FPGAs), and/or one or more application-specific integrated circuits (ASICs).

The memory 414 includes volatile memory (e.g., RAM including non-volatile RAM, magnetic RAM, ferroelectric RAM, etc.), non-volatile memory (e.g., disk memory, FLASH memory, EPROMs, EEPROMs, memristor-based non-volatile solid-state memory, etc.), unalterable memory (e.g., EPROMs), read-only memory, and/or high-capacity storage devices (e.g., hard drives, solid state drives, etc.), and/or combinations thereof. The memory 414 is computer readable media on which one or more sets of instructions, such as the software for operating the methods of the present disclosure, can be embedded. For example, the instructions may embody one or more of the methods or logic as described herein.

The communication device(s) 430 include hardware (e.g., processor(s), memory, storage, antenna(s), etc.), software, and wired and/or wireless network interface(s) to enable communication with other server(s) (e.g., the pin drop server 300), device(s) and/or network(s) to control the wired or wireless network interfaces. Example external network(s) include a public network, such as the Internet; a private network, such as an intranet; or combinations thereof, and utilize one or more networking protocol(s) for communication.

The input device(s) 440 of the illustrated example enable an operator, such as a programmer for the Carto server 400, to provide instructions, commands, and/or data to the Carto controller 410. Examples of the input device(s) 440 include one or more of a button, a control knob, an instrument panel, a touch screen, a touchpad, a keyboard, a mouse, a speech recognition system, etc.

The output device(s) 450 of the illustrated example display output information and/or data of the Carto controller 410 to an operator, such as a programmer for the pin drop server 300. Examples of the output device(s) 450 include a display (e.g., a liquid crystal display (LCD), an organic light emitting diode (OLED) display, a flat panel display, etc.) and/or any other device that visually presents information to an operator. Additionally or alternatively, the output device(s) 450 may include one or more speakers and/or any other device(s) that provide audio signals for an operator. Further, the output device(s) 450 may provide other types of output information, such as haptic signals.

FIGS. 6-9 are flowcharts of an example method 500 for generating an interactive visualization of health information. The flowcharts of FIGS. 6-9 are representative of machine readable instructions that are stored in memory (such as the memory 214 of FIG. 3, the memory 314 of FIG. 4, and/or the memory 414 of FIG. 5) and include one or more programs which, when executed by processor(s) (such as the processor(s) 212 of FIG. 3, the processor(s) 312 of FIG. 4, and/or the processor(s) 412 of FIG. 5), cause the visualization system 100 to generate an interactive visualization of health information. While the example program is described with reference to the flowcharts illustrated in FIGS. 6-9, many other methods of generating an interactive visualization of health information may alternatively be used. For example, the order of execution of the blocks may be rearranged, changed, eliminated, and/or combined to perform the method 500. Further, because the method 500 is disclosed in connection with the components of FIGS. 1-5, some functions of those components will not be described in detail below. To the extent one or more flowcharts depicts steps performed in series, one of ordinary skill would appreciate that the steps can be also be performed in parallel.

Figure 6:
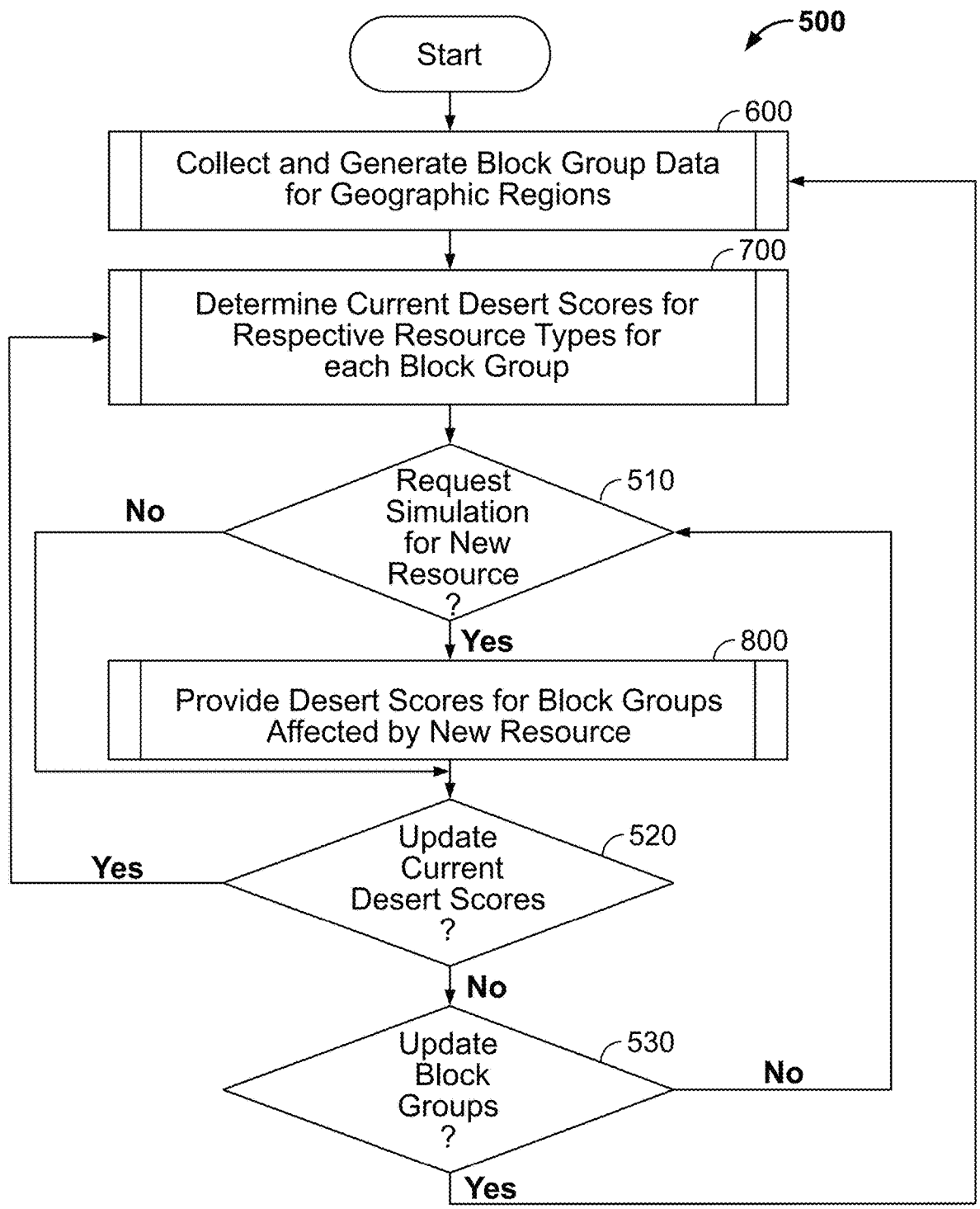
FIG. 6 is an example flowchart for generating an interactive visualization of health information according to the instant disclosure.

Turning to FIG. 6, method 500 of visualization system 100 includes the steps of: (1) performing a baseline desert score for all of the block groups across the U.S., (2) receiving user requests for new resources, and (3) calculating, in real-time, a new desert score for block groups affected by the new resource(s). In various embodiments, pin drop controller 310 performs each of the steps of method 500. In other embodiments, other device(s) of visualization system 100 perform one or more steps of method 500.

For example, in one embodiment visualization system 100 at step 600 collects and generates block group data for all of the block groups across the U.S. At step 700, visualization system 100 determines the baseline or current desert scores for respective resource types for each block group. At step 510, visualization system 100 may receive a request to simulate the effect of a new resource placed at a user-selected geographic location in the U.S. In response, visualization system 100 at step 800 computes new desert scores for block groups in the immediate or nearby vicinity of the block group(s) in which the new resource(s) are located. At step 520, visualization system 100 updates one or more databases associated with visualization system 100, and at step 530, visualization system 100 may store updated block group data in the one or more databases. At step 520, if the visualization system 100 receives a new or changed census data set with new resources having physically been built or previously existing resources having been torn down, then visualization system 100 is configured to allow recalculation of current desert scores at step 700 before another simulation is run at step 510. Likewise at step 530, if the visualization system 100 receives a new or changed census data set with new or changed block group data, such as new or changed block groups or new or changed data representing the sphere of daily economic activity for such new or changed block groups, then visualization system 100 is configured to allow repeat step 600 to collect and generate block group data for all of the block groups across the U.S., and recalculate the current desert scores at step 700 before another simulation is run at step 510.

Figure 7:
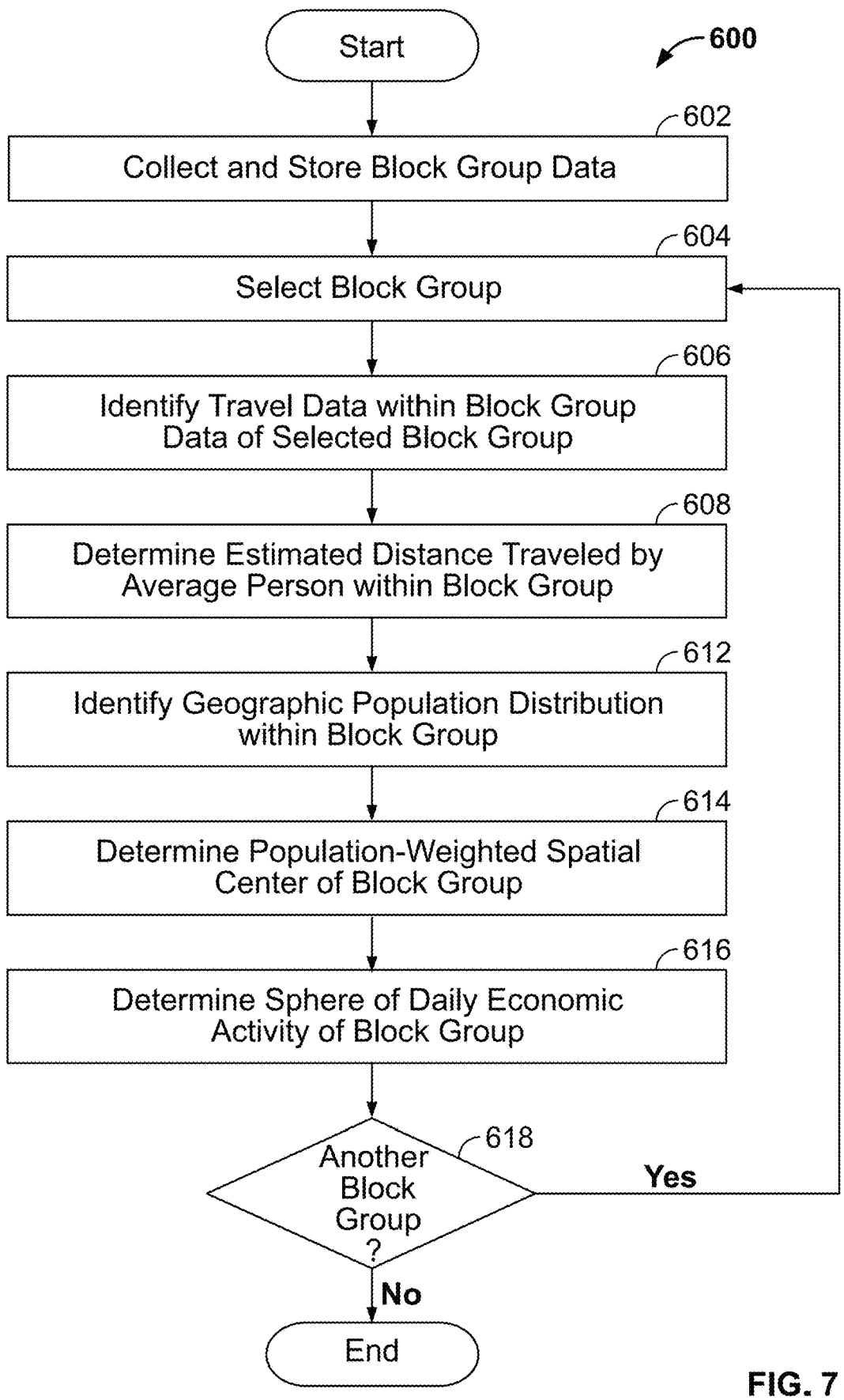
FIG. 7 is an example flowchart for collecting and generating block group data of geographic regions within the flowchart of FIG. 6.

FIG. 7 is a flowchart that depicts an example method 601 for performing step 600 of FIG. 6. Visualization system 100 at step 602 collects and stores block group data for all of the block groups across the U.S. At steps 604 and 606 for each block group, visualization system 100 identifies population travel data within the block group data for each block group. At step 608 and for each block group, visualization system 100 determines the estimated distance traveled by people residing in the block group. As previously mentioned, the population travel data for each block group and the estimated distance traveled by people residing in each block group may be derived from the Commuting (Journey to Work) section of the American Community Survey that the U.S. Census Bureau collects, compiles, and makes available to the public. At step 612, visualization system 100 is configured to determine the geographic population distribution within each block group, and using that information at step 614, visualization system 100 is configured to determine the population-weighted latitudinal and longitudinal center (also called, the population-weighted spatial center) of each block group. Many block groups include relatively large unsettled regions of land (e.g., lakes, parks, farmland, etc.). Visualization system 100 determines the population-weighted spatial center to more accurately evaluate how people act within a block group that has a geographically uneven distribution of residents. To determine the population-weighted spatial center, visualization system 100 uses block-level population and coordinate data of all the blocks within a block level. Visualization system 100 weights the population and coordinate data of each block within the block level to find the population-weighted spatial center of the block group.

Figure 10:
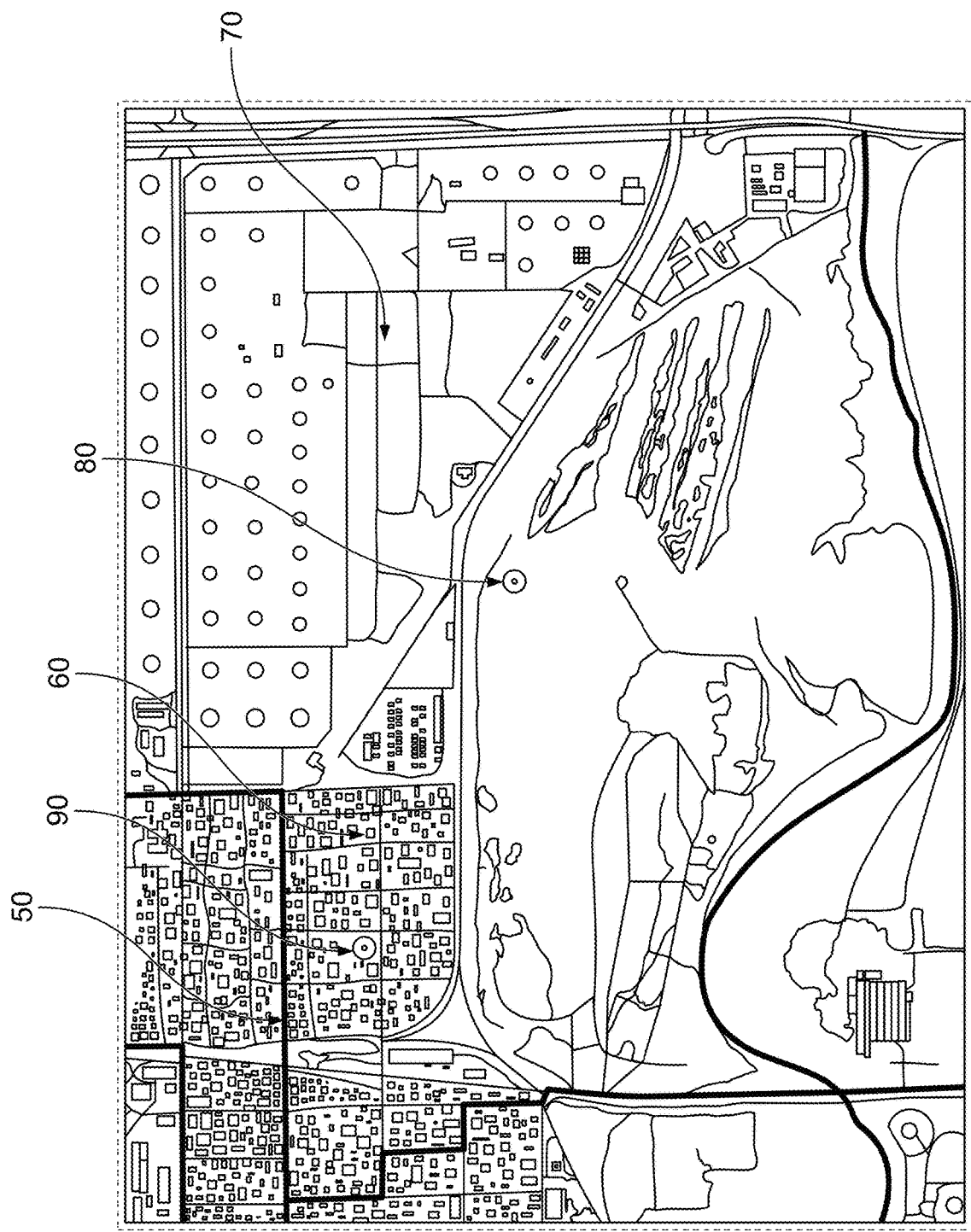
FIG. 10 depicts a geographic map of an example block group.
Figure 11:
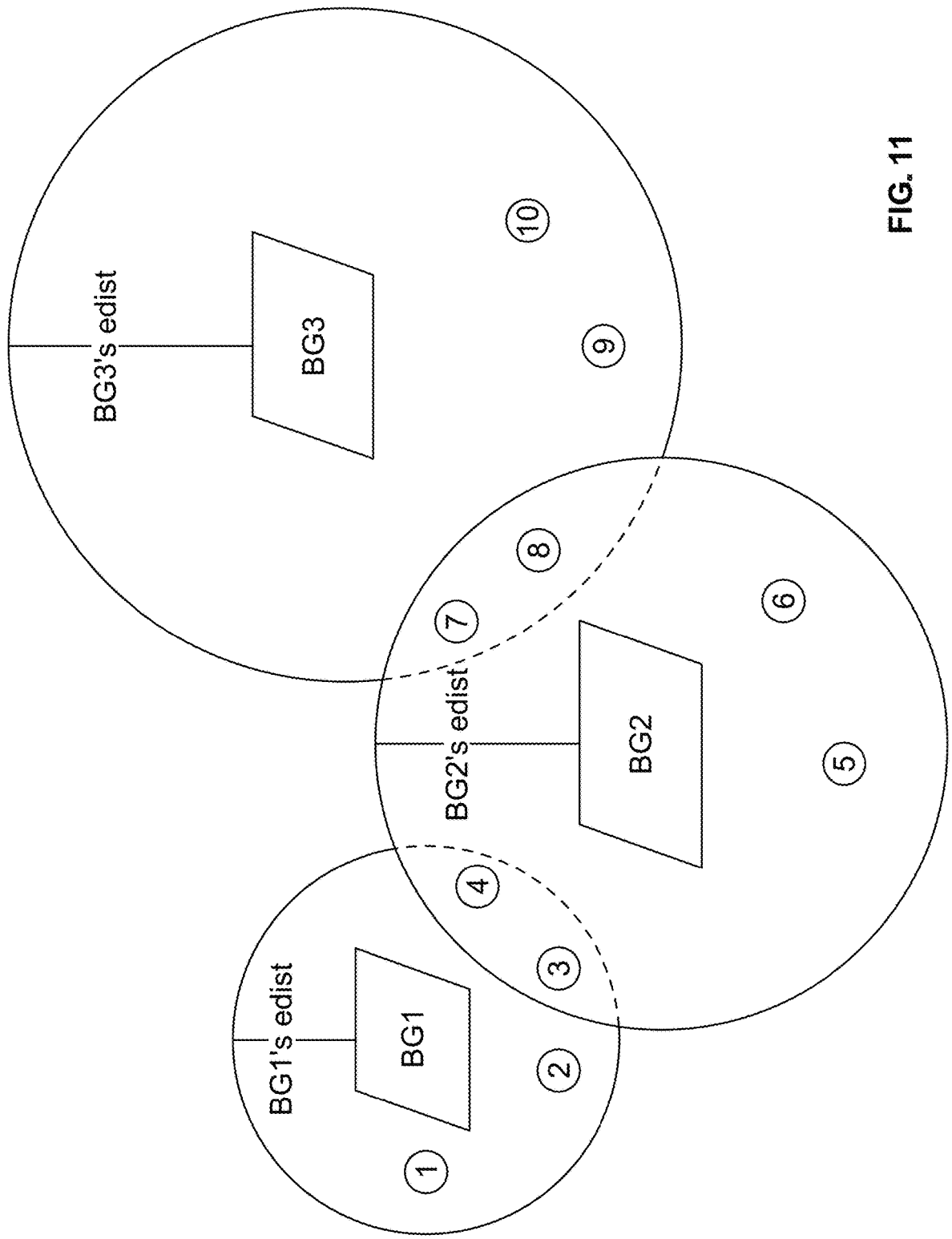
FIG. 11 depicts a representation of adjacent block groups, respective spheres of daily economic activity derived from the average distances of travel by people in the respective block groups, and resources the lie within each block group.

Knowing the population-weighted spatial center of each block group and the average distance traveled across all major modes of transportation by the population of each block group, visualization system 100 may determine the sphere of daily economic activity by people in each block group. In various embodiments, for each block group the sphere of daily economic activity is equal to the geographic area circumscribed by a circle having its center at the population-weighted spatial center and a radius equal to the average distance traveled by people in each respective block group. FIG. 11 schematically illustrates exemplary block groups having different spheres of daily economic activity of their respective residents due to the different average distances traveled by people in each respective block group. FIG. 10 illustrates one example of how the population-weighted spatial center of a block group may differ from the geometric centroid of the block group. For example, the irregular-shaped boundaries of block group 50 are shown for a particular block group in the outskirts of the Chicago, IL geographic area. This particular block group is characterized by a densely populated area 60 in the upper left quadrant of block group 50, and large areas of nonpopulated space 70 in the other three quadrants of block group 50. In this example, the geospatial center or centroid 80 of block group 50 lies in the open space 70 of block group 50. By comparison, the population-weighted spatial center 90 lies within the spatial center of the populated region of block group 50. By using the population-weighted spatial center 90, and not the geospatial center, from which to compute the sphere of daily economic activity for block group 50, a more accurate computation of the desert scores can be achieved.

Figure 8A:
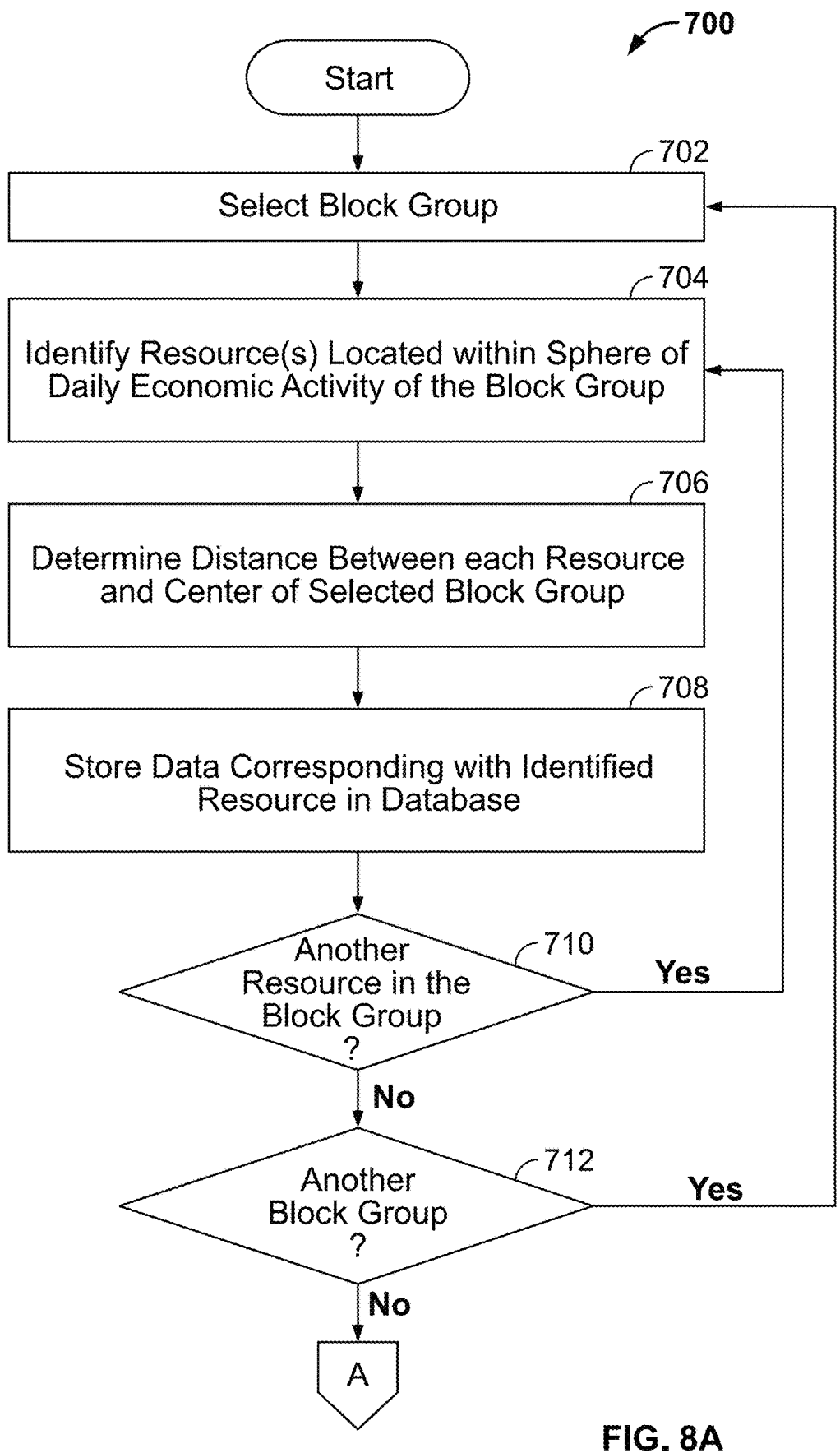
FIGS. 8A-8B are an example flowchart for determining current desert scores for respective resource types within block groups within the flowchart of FIG. 6.
Figure 8B:
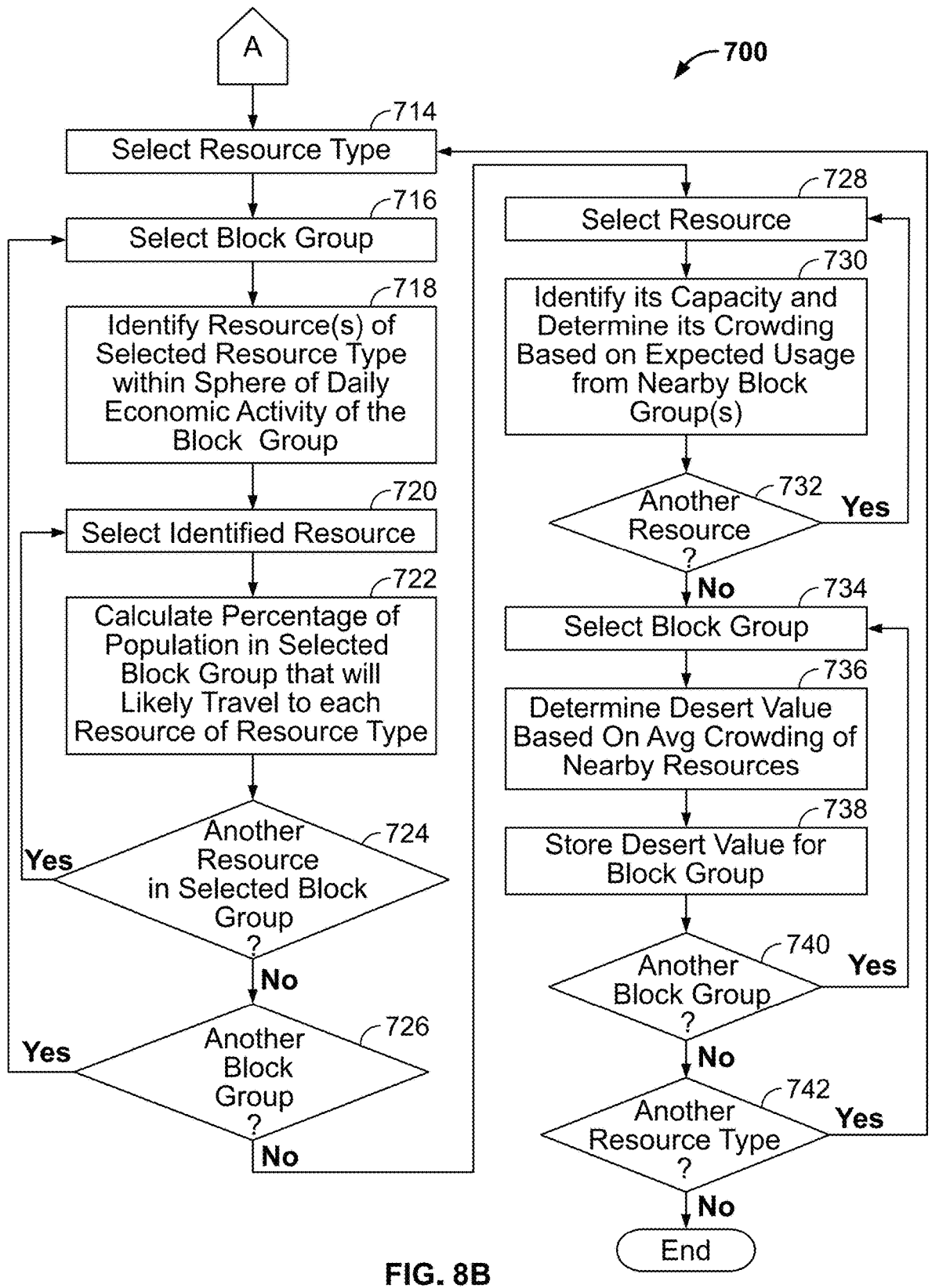

FIGS. 8A-8B is a flowchart that depicts an example method 701 for performing step 700 of FIG. 6. At steps 702 and 704 for each block group, visualization system 100 identifies each and every resource that lies within the sphere of daily economic activity for people in each respective block group. To do that, visualization system 100 may be configured to utilize a PostGIS function to find all of the resources for a given block group that lie within the circle circumscribed by the radius that is equal to the average distance traveled by people in each respective block group.

At step 706, visualization system 100 is configured to determine the distance between each resource lying within the sphere of daily economic activity and the population-weighted spatial center of each block group. Visualization system 100 may utilize a Postgres function, which leverages the haversine formula, to calculate the raw distance in miles between the latitudinal and longitudinal coordinates of the population-weighted spatial center of each block group and each resource. In various embodiments, a relative distance ("rdist") may be computed by (1−raw distance/average distance traveled by the population in the block group). Thus, resources with an rdist close to 1 are very close to the population-weighted spatial center of the block group and resources with an rdist close to 0 are close to the outer edge of the sphere of daily economic activity for each block group.

At step 708, visualization system 100 is configured to store the data corresponding with each identified resource in at least one of the databases associated with the system. At steps 710 and 712, the process is shown to continue/repeat until all of the data corresponding to each resource for each block group across the United States is stored in the database.

At this point, the desert scores for each of the known pre-existing block groups can be calculated. For each resource type at step 714 and for each block group at step 716, visualization system 100 is configured at step 718 to identify the resources that are accessible to people in each block group. At steps 720 and 722 for each identified resource, visualization system 100 is configured to calculate the percentage of people in each block group that will likely travel to each resource. To do that, visualization system 100 may be configured to distribute the population in each block group to all of the block group's accessible resources by a cubic decay function. In this way, a larger proportion of a block group's population may be assumed to be able to access nearby resources (i.e., closer to the population-weighted spatial center of the block group) rather than further resources (i.e., closer to the circular perimeter of the block group defined by the average distance traveled by the population). At steps 724 and 726, the process is shown to continue/repeat until the percentage of people in each block group that will likely travel to all of the resources for each block group across the United States are computed.

FIG. 11 illustrates how the cubic decay function may apply to block groups. There are shown, for example, three block groups BG1, BG2, and BG3, with BG1 adjacent to BG2, and BG2 is adjacent to BG3. The sphere of daily economic activity is larger for BG3 than BG2, and sphere of daily economic activity is larger for BG2 than BG1—all as defined by the average distance traveled by people in each respective block group (i.e., which is equal to the radius of each circle, also known as their respective edist). Within each sphere of daily economic activity lies one or more resources labeled 1 through 10, respectively. Thus, in this example, resources 1 through 4 lie within the sphere of daily economic activity for BG1, resources 3 through 8 lie within the sphere of daily economic activity for BG2, and resources 7 through 10 lie within the sphere of daily economic activity for BG3. From this, it can be said that BG1 intersects with resources 1 through 4, BG2 intersects with resources 3 through 8, and BG3 intersects with resources 7 through 10. In addition, as seen in this example, BG2 shares resources 3-4 with BG1 and BG2 shares resources 7-8 with BG3.

For purposes of this example, it is assumed that the rdists for BG1 and resources 1, 2, 3 and 4 are 0.9, 0.63, 0.2, and 0.2, respectively. By cubing each of the rdists, the values now become 0.729, 0.25, 0.008, and 0.008, respectively. Summing these values results in the percentage of the population that are likely to travel to each resource. In this example, the values sum to 0.995 and the population weights become 0.733, 0.251, 0.008, and 0.008, respectively. Thus, 73.3% of BG1's population will travel to resource 1 since it is the closest, and 0.8% of the population will travel to resource 4 since it is the furthest.

Steps 728 through 742 allow visualization system 100 to take into account the number of people who travel to shared resources. For example, for every resource across the United States, visualization system 100 at steps 728, 730, and 732 identifies the capacity of the resource and determines a measure of crowding of, or usage levels by, people at each resource_including people from nearby block groups. The measure of crowding may be determined by taking the sum of people that access the resource, including people from nearby block groups where resources are shared by populations from multiple block groups who can access the resources and dividing by the capacity of each resource. As a proxy, visualization system 100 may assume the capacity of the resource is equal to the total number of employees at the resource. This process results in a measure of crowding of accessible resources by taking the population-weighted average crowding at their accessible resources. Additional adjustments can take into account community-level variations, such as college campuses, military bases, and the like.

Because populations in each block group tends to affect resources in nearby block groups, it is not efficient to compute desert scores one block group in isolation. Conversely, calculating all of the block groups across the United States at the same time requires substantial memory resources and processor speed. The solution to this dilemma is to compute the desert scores of a block group in relation to nearby block groups. But even this solution results in approx. 100 million block group-resource intersections and requires about 48 hours to compute the desert scores. Thus, for each block group at steps 734 and 736, visualization system 100 determines the desert scores based on the measure of crowding as set forth above. The desert score of a block group reflects the average crowding conditions among nearby resources weighed by the share of block group population attributed to each resource. In various embodiments, visualization system 100 modifies an aggregate measure of scarcity for a block group to take into account populations that are not normally interacting with public resources (e.g., college students, military personnel, the incarcerated, etc.) and/or populations with limited or no access to a vehicles. In various embodiments, visualization system 100 adjusts the distribution of scores to fit a lognormal distribution. At step 738, visualization system 100 is configured to store the desert score for each block group in at least one of the databases associated with visualization system 100. At steps 740 and 742, the process is shown to continue/repeat until the desert scores for all of the resources and for all of the block groups have been computed and stored, thus completing the baseline desert score computation for all block groups across the United States.

To account for new resources interactively placed anywhere on the map of the United States, visualization system 100 may be configured to receive (1) a selection from the user regarding the type of resource of interest to be modeled, and (2) a selection from the user regarding the geographic location in the United States for which a new resource of the selected type should be located. To avoid having to recalculate all of the block groups across the United States at the same time to account for the new resource as well as the demand by people who can access the resource as well as the decreased demand on pre-existing nearby resources, visualization system 100 may be configured to compute new desert scores but only for those block groups that are directly or secondarily affected by the additional resource. In addition, as illustrated in FIGS. 2 and 4 above, visualization system 100 may store the required data quickly in the SQLite database 330 as an in-memory database to enable faster read times, which is where most of the time may be spent when calculating new desert scores.

Figure 9:
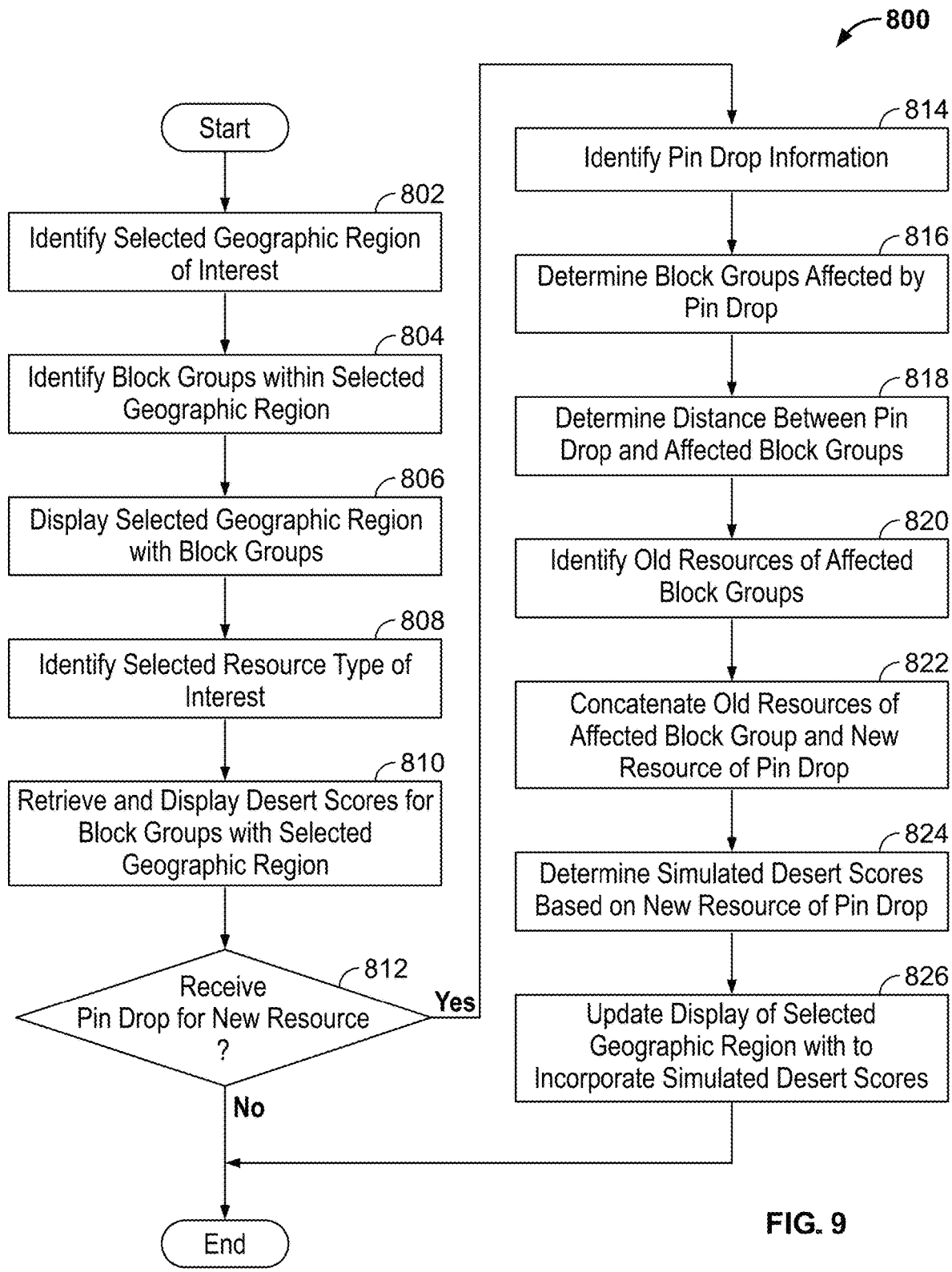
FIG. 9 is an example flowchart for providing new desert scores for block groups affected by a new resource within the flowchart of FIG. 6.

FIG. 9 is a flowchart that depicts an example method 800 for computing the new desert scores for each block group that is primarily and secondarily affected by the addition of a new, nearby resource. As a starting point, it is assumed that each block group across the U.S. has an original, baseline desert score pertaining to each resource type. Data associated with each block group's desert score may be stored in one of the databases associated with visualization system 100, such as the SQLite database 330 or the Carto database 420. For example, the SQLite database 330 may be useful in computing new desert scores and to save them in memory along with all of the block group resource intersections. The Carto database 420 and or its related components may be used to visualize the baseline desert score and the new desert score while utilizing the CHM hub controller 210 for rendering the image in a displayable form for the user. The Carto database 420 can be configured to store all block group data and the original block group desert scores.

At step 802, visualization system 100 is configured to identify a selected geographic region of interest requested by a user. At step 804, visualization system 100 is configured to identify all of the block groups that lie within the selected geographic region of interest. At step 806, visualization system 100 may provide instructions that are carried out by the user's browser to display the selected geographic region together with a rendering of the block groups that are visible at the selected zoom level and for the selected geographic region.

In one example, the CHM hub controller 210 may detect and identify the zoom level of the map displayed on the user's computer display as well as the geographic region of the U.S. that is displayed on the user's display. The CHM hub controller 210 may also be configured to provide instructions for displaying a map of the U.S. at the user-selected zoom level and geographic region. As shown in FIG. 2, pin drop controller 310 may be configured to receive the user's selections for zoom level and geographic region and provide the CHM hub controller 210 with block group and desert score information for display on the user's display.

At step 808, visualization system 100 is configured to receive and identify a selection from the user regarding the type of resource of interest to be modeled or simulated. At step 810, visualization system 100 is configured retrieve and provide to for display on the user's display the desert scores for the block groups that are visible at the selected zoom level and for the selected geographic region.

At step 812, visualization system 100 is configured to receive a selection from the user regarding the geographical location of a new resource of the type previously selected. The user may select multiple locations for new resources to be located. In various embodiments, the act by the user to make their selection of the location for the new resource is akin to dropping a pin on the map, and is accomplished by clicking a mouse at the desired location, for example. At step 814, visualization system 100 is configured to receive the latitudinal and longitudinal coordinates of the user's geographical placement and/or other information (e.g., resource type, resource capacity, etc.) of the new resource(s) and store this data on, for example, the PostgreSQL database 320 and/or the SQLite database 330.

In response to receiving the new resource and new location data, visualization system 100 at step 816 is configured to determine which block groups are affected by the addition of the new resource. The affected block groups include primary, secondary, and tertiary block groups. A primary block group has an edist that intersects with a new resource. For example, visualization system 100 uses the haversine formula to compare the latitudinal and longitudinal coordinates of a new resource to the latitudinal and longitudinal coordinates of the population-weighted spatial center of each block group to identify which block groups intersect with the new resource. A secondary block group does not have an edist that directly intersects with a new resource, but shares resources with a primary block group. A new resource may decrease the desert score of a secondary block group desert score, even though the secondary block group does not directly intersect with the new resource, by decreasing crowding at other resources near the new resource (e.g., within the secondary block group). A tertiary block group does not intersect with a new resource or with resources that fall within a primary block group's resources. In turn, a tertiary block group is not impacted by the new resource and its desert score does not change.

The PostgreSQL database 320 finds the affected block groups using a PostGIS ST_Intersection( ) routine. The ST_Intersection( ) routine can return geometry representing the point-set intersection of two geometries to that overlap with one another. At step 818, the PostgreSQL database 320 of visualization system 100 is configured to determine the raw distance between the latitude/longitude coordinates of the new resource and the population-weighted spatial centers of the affected block groups. The PostgreSQL database 320 finds the raw distance between new pins and affected block groups using a PostGIS ST_Distance( ) routine. The ST_Distance( ) routine can return the minimum 2D Cartesian (planar) distance between two geometries, in projected units (spatial reference units). The PostgreSQL database 320 may transmit the affected block group data and the raw distance data to the pin drop controller 310.

Knowing the raw distance and the length of each radius that relates to the average travel distances of people in the block groups, visualization system 100 may be configured to compute the relative distance as described above using Python coding.

At step 820, visualization system 100 is configured to identify all of the pre-existing resources that lie within the affected block groups. In various embodiments, pin drop controller 310 is configured to transmit the affected block group data to the SQLite database 330 to find the pre-existing resources that lie within the affected block groups. Upon completion of that task, the SQLite database 330 may be configured to transmit the pre-existing resource data to the pin drop controller 310. At step 822, the visualization system 100 is configured to concatenate the new resource data and the pre-existing resource data for all of the affected block groups. In various embodiments, the pin drop controller 310 is configured to perform this task.

At step 824, visualization system 100 is configured to compute new desert scores for the concatenated new resource data and the pre-existing resource data for all of the affected block groups. In various embodiments, visualization system 100 is configured to compute a percent change between the new desert scores and the original desert scores for all of the affected block groups. For example, visualization system 100 calculates (e.g., uses coding such as Python) the percent change for a respective block group based on the formula of Percent_Change=(Original_Desert_Score—New_Desert_Score)/Original_Desert_Score. In various embodiments, the pin drop controller 310 is configured to transmit the new block group desert scores to the Carto database 420 for storing and rendering. The Carto database 420 can be configured to create a new layer containing the new desert scores for the affected block groups and an updated data table for transmission to the user's computer display via, for example, the CHM hub controller 210. The Carto database 420 can also be configured to create a new layer containing the percent change between the new and original desert scores for the affected block groups and configured to create an updated data table for transmission to the user's computer display via, for example, the CHM hub controller 210. At step 826, the new resource desert scores and accompanying data are transmitted by visualization system 100 to the user for display. In various embodiments, visualization system 100 is configured to enable user 20 to toggle between viewing the store pin information and the percent change of the affected block groups via display 15 of remote computer 10.

Figure 12:
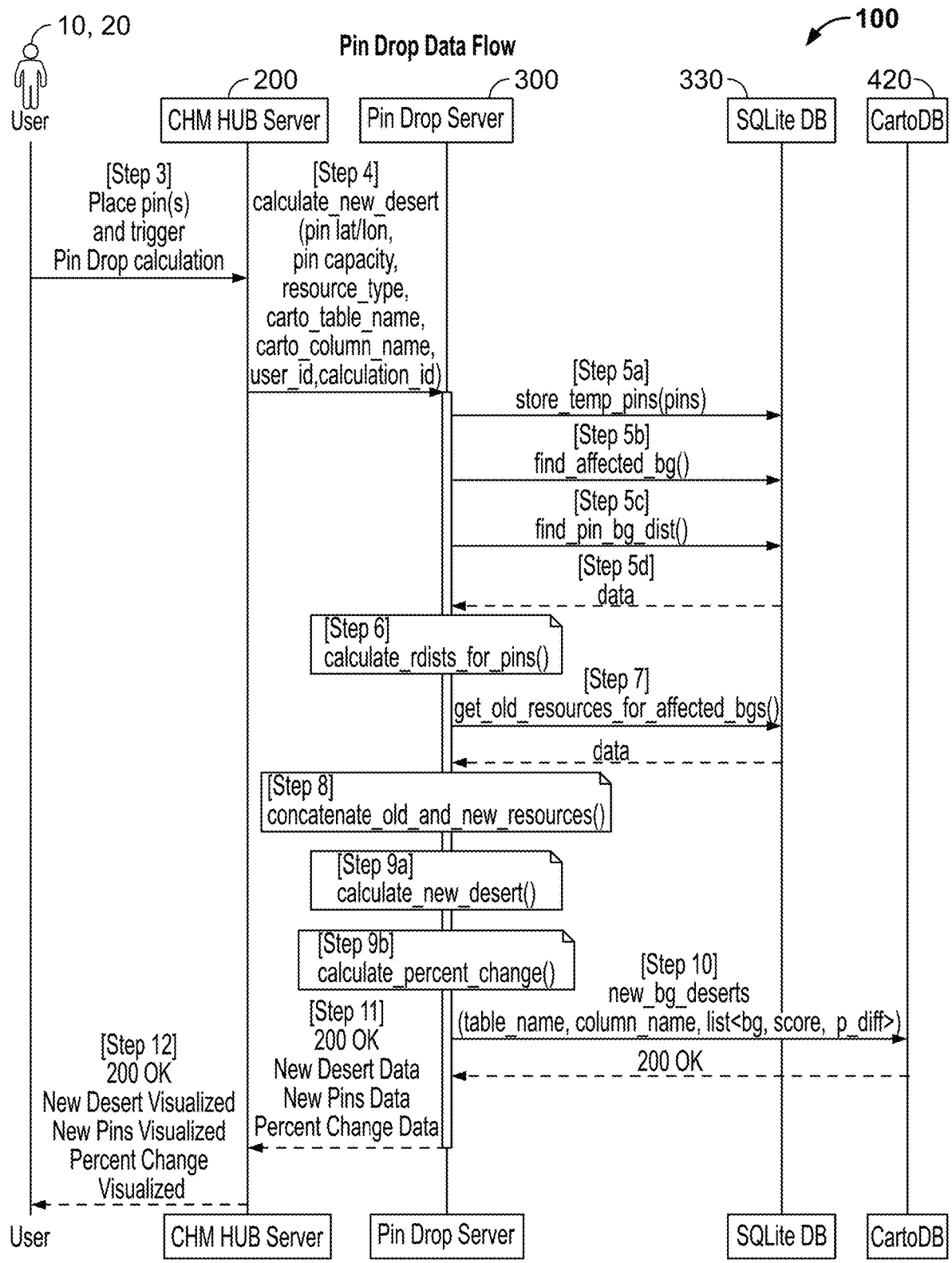
FIG. 12 depicts a diagram illustrating one embodiment of the instant disclosure for providing desert scores for block groups affected by a new resource in accordance with the flowchart of FIG. 9.

Turning to FIG. 12 there is shown an example ULM diagram describing the data flows between the various components of visualization system 100 and user 20, including for the computation of the new desert scores. At step 3, CHM hub server 200 is configured to receive pin locations indicative of new resources for visualization system 100 to simulate. At step 4, pin drop server 300 receives the request to calculate new desert scores based on the latitude and longitude of the new resources as well as the capacity of each new resource in terms of the number of estimated employees, where an employee count of 1 is suggestive of a new convenience store resource with limited nutritional options available to customers who can access the new resource and where an employee count of 50 is suggestive of a new grocery store resource with a wider array of nutritional options. At steps 5a-5d, the PostgreSQL database 320 is configured to temporarily store the new resource locations (step 5a), determine the affected block groups (step 5b), determine the raw distances between the latitude/longitude coordinates of the new resources and the population-weighted spatial centers of the affected block groups (step 5c), and transmit the affected block data and the raw distance data to pin drop server 300 (step 5d). At step 6, pin drop server 300 is configured to determine the relative distances between the new resources and the population-weighted spatial centers of the affected block groups. At step 7, the SQLite database 330 is configured to identify all of the pre-existing resources that lie within the affected block groups. Upon completion of that task, the SQLite database 330 may be configured to transmit the pre-existing resource data to the pin drop server 300. At step 8, pin drop server 300 is configured to concatenate the new resource data and the pre-existing resource data for all of the affected block groups. At step 9a, pin drop server 300 is configured to calculate, in real-time, the new desert scores for the affected block groups. At step 9b, pin drop server 300 is configured to calculate, in real-time, a percent change between the new desert scores and the existing desert scores for the affected block groups. At step 10, Carto server 400 is configured to receive the new desert scores, percent changes, and/or other block group information from the pin drop server 300, and Carto database 420 is configured to store the block group information. Carto server 400 also is configured to prepare an overlay of the new desert scores for display on the user's display 15. The overlay includes any adjustments to the colors for the affected block groups to allow the user to readily ascertain the impact of the simulated placement of the new resources. In other embodiments, instead of rendering colors to designate desert scores, the Carto server 400 may be configured to render the block groups in different shading, stippling, and the like to convey to the user differences in desert scores for the visible block groups. Upon completion of the rendering instructions, the pin drop server 300 is configured to receive the rendering instructions from the Carto server 400. In this example, at step 11 the CHM hub server 200 is configured to receive the rendering instructions from the pin drop server 300 and to transmit those instructions for display in a web browser on the user's display 15.

Figure 13:
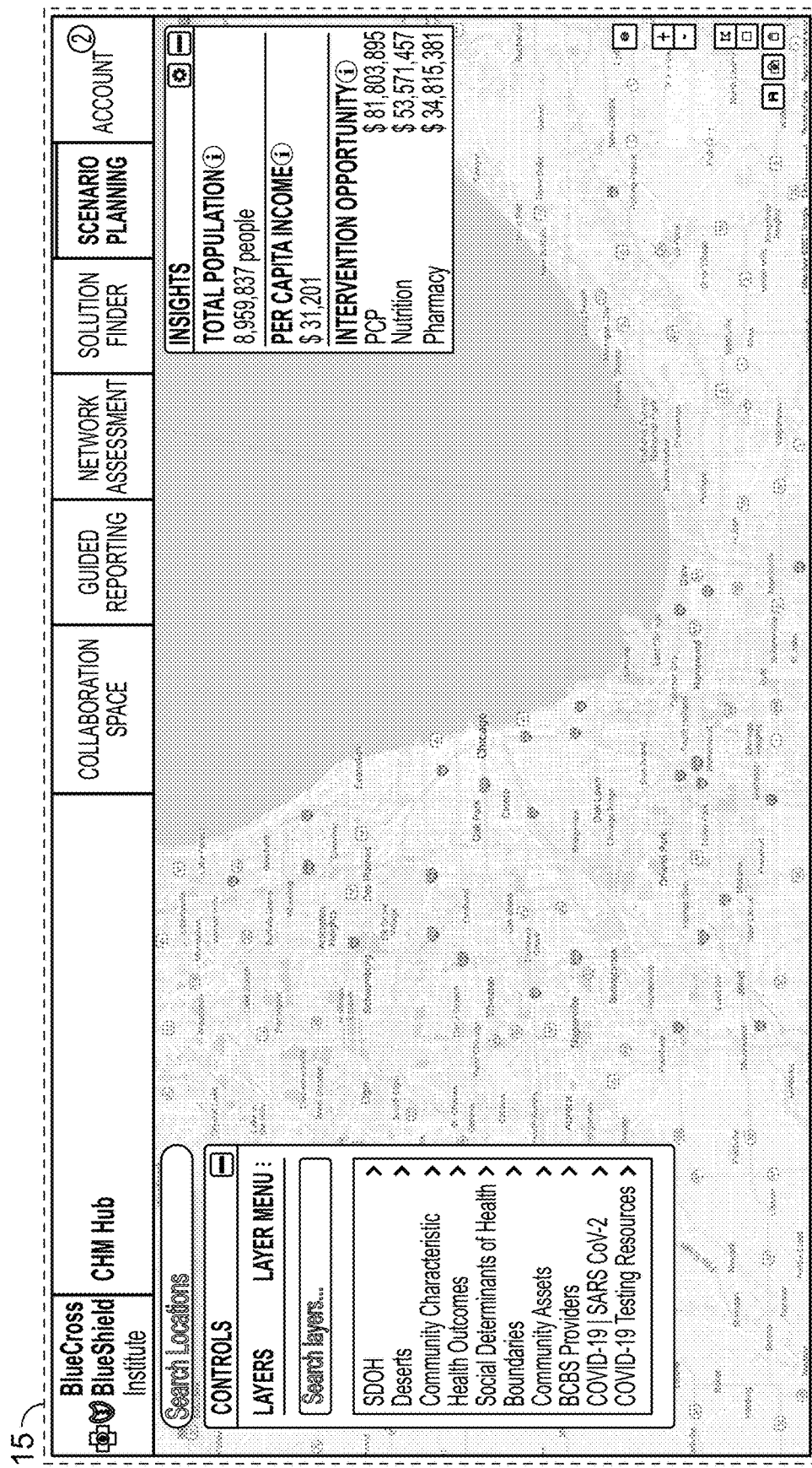
FIG. 13 depicts an example interface for a user of the visualization system of FIG. 1.
Figure 14:
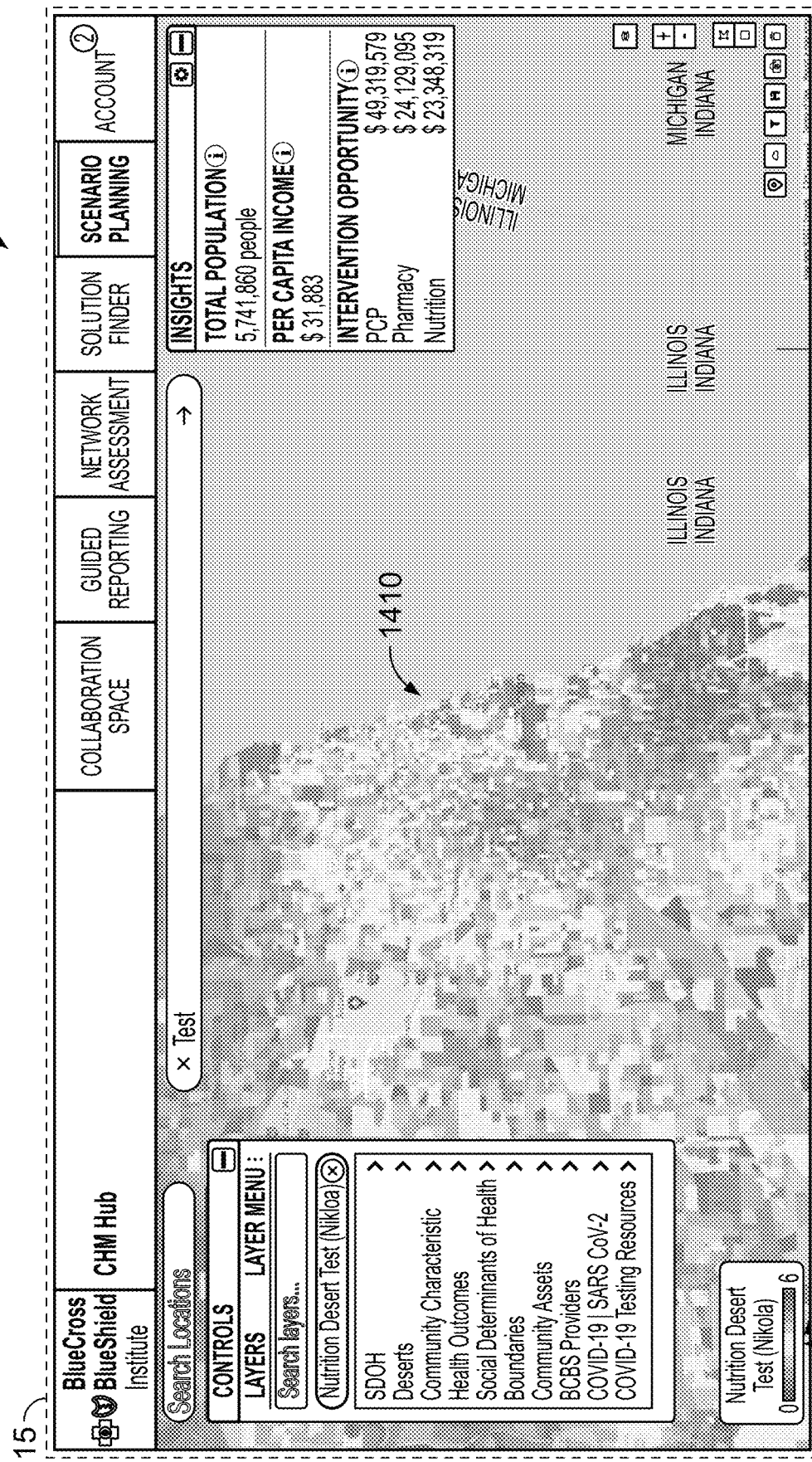
FIG. 14 depicts another example interface for a user of the visualization system of FIG. 1.
Figure 15:
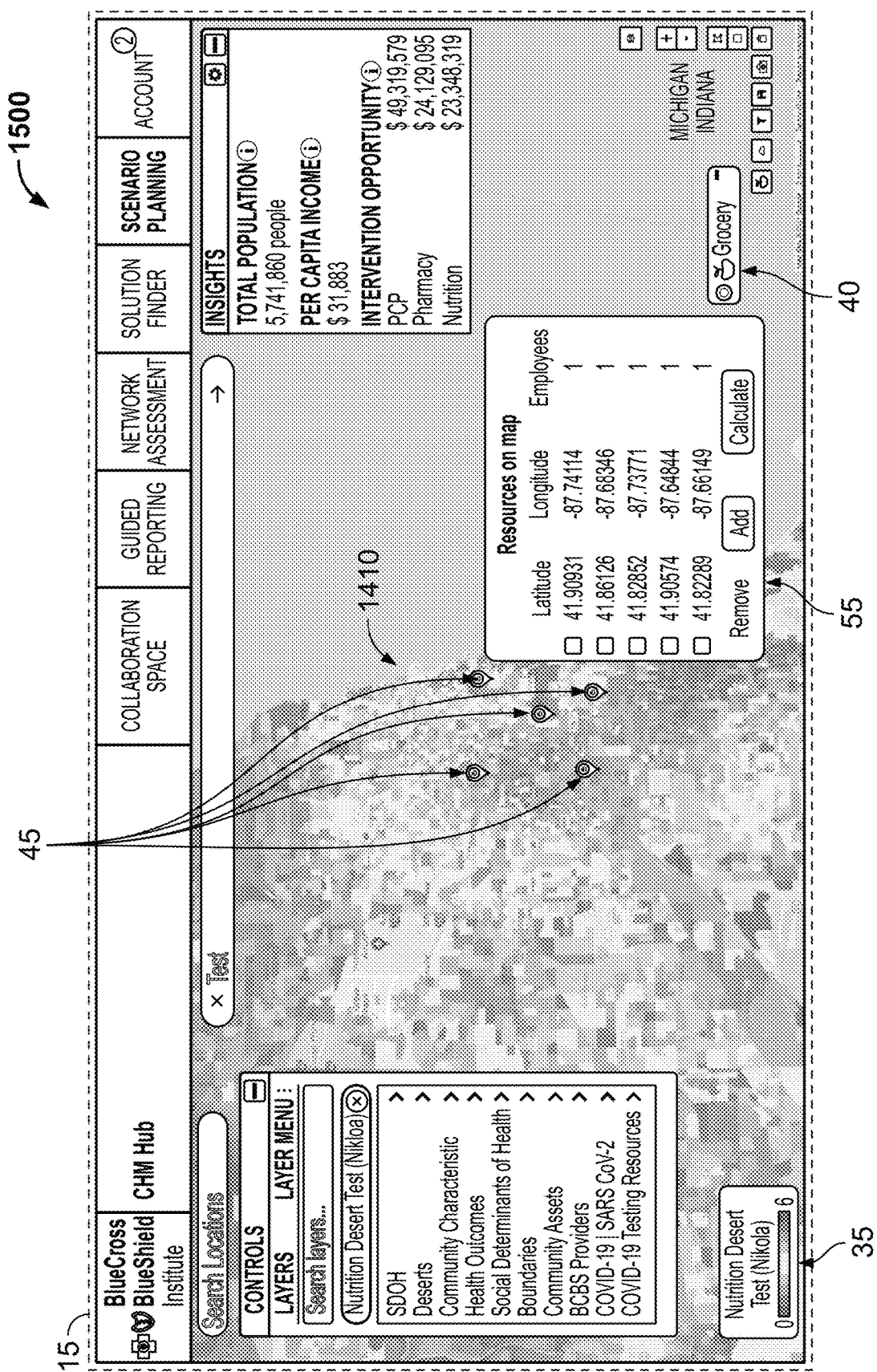
FIG. 15 depicts another example interface for a user of the visualization system of FIG. 1.
Figure 16:
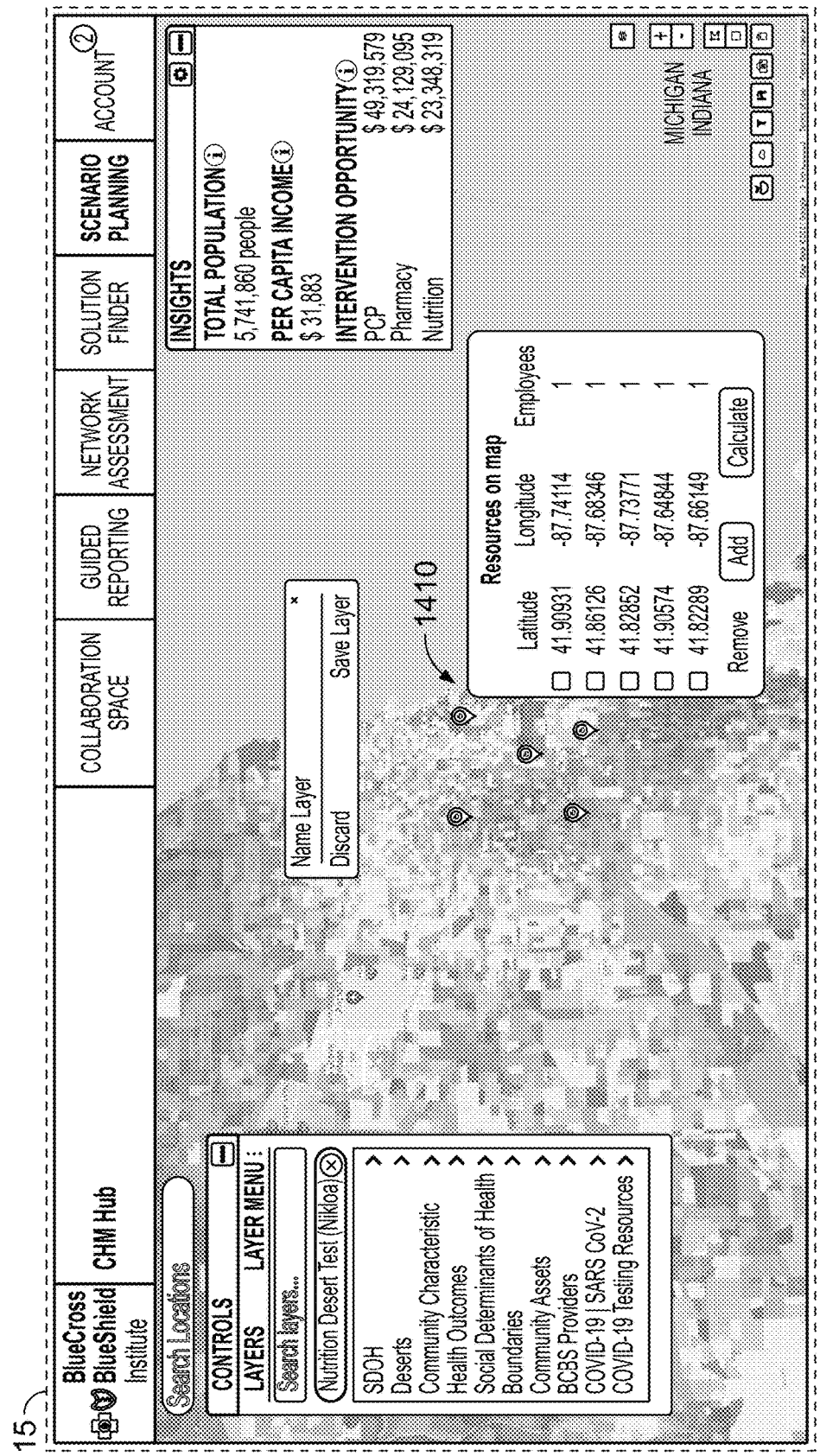
FIG. 16 depicts another example interface for a user of the visualization system of FIG. 1.

FIGS. 13-16 show example images that are visible to the user on the user's display 15. FIG. 13 shows an interface 1300 that includes a geographic image of the Chicago metropolitan area at a zoom level chosen by the user. FIG. 14 shows an interface 1400 that includes a slightly higher zoom level as the same image of FIG. 13 together with hundreds of different block groups 1410 overlaid on the map. The different block groups 1410 are illustrated in different geometric shapes as determined by the U.S. Census Bureau. The colors of the different block groups 1410 represent the different initial desert scores associated with each of the block groups. In this way, a user can quickly identify according to legend 35 areas where nutritional deserts, for example, exist in the Chicago metropolitan area. The user may select a toggle switch, button, drop down, or other object/device in interface 1400 to change the mode of operation to pin drop mode. In this mode, visualization system 100 may numerically compute and graphically display the impact of the addition or removal of any number of resources on the desert score according to the systems and methods of the instant disclosure. FIG. 15, for example, shows an interface 1500 that includes the same image of FIG. 14 after visualization system 100 receives the user's selection of "grocery" type 40 placement of one or more new resources 45 (in this illustration, 5 new "grocery" type resources) at various locations on the map with the goal of simulating how the placement of those resources 45 would affect the desert scores of the block groups 1410 affected by the simulated existence of those resources. The tabular data in legend 55 illustrates the detected latitude and longitude of each of the new resources 45 as well as the estimated number of employees at each new resource 45. FIG. 16 shows an interface 1600 that includes the same image of FIG. 15 after real-time completion of new desert scores of the block groups 1410 by visualization system 100 according to the teachings herein.

One of ordinary skill would appreciate that visualization system 100 may be configured to compute the new desert scores for block groups affected by the removal of one or more resources in much the same way that visualization system 100 computes the new desert scores for the addition of one or more new resources.

Figure 17:
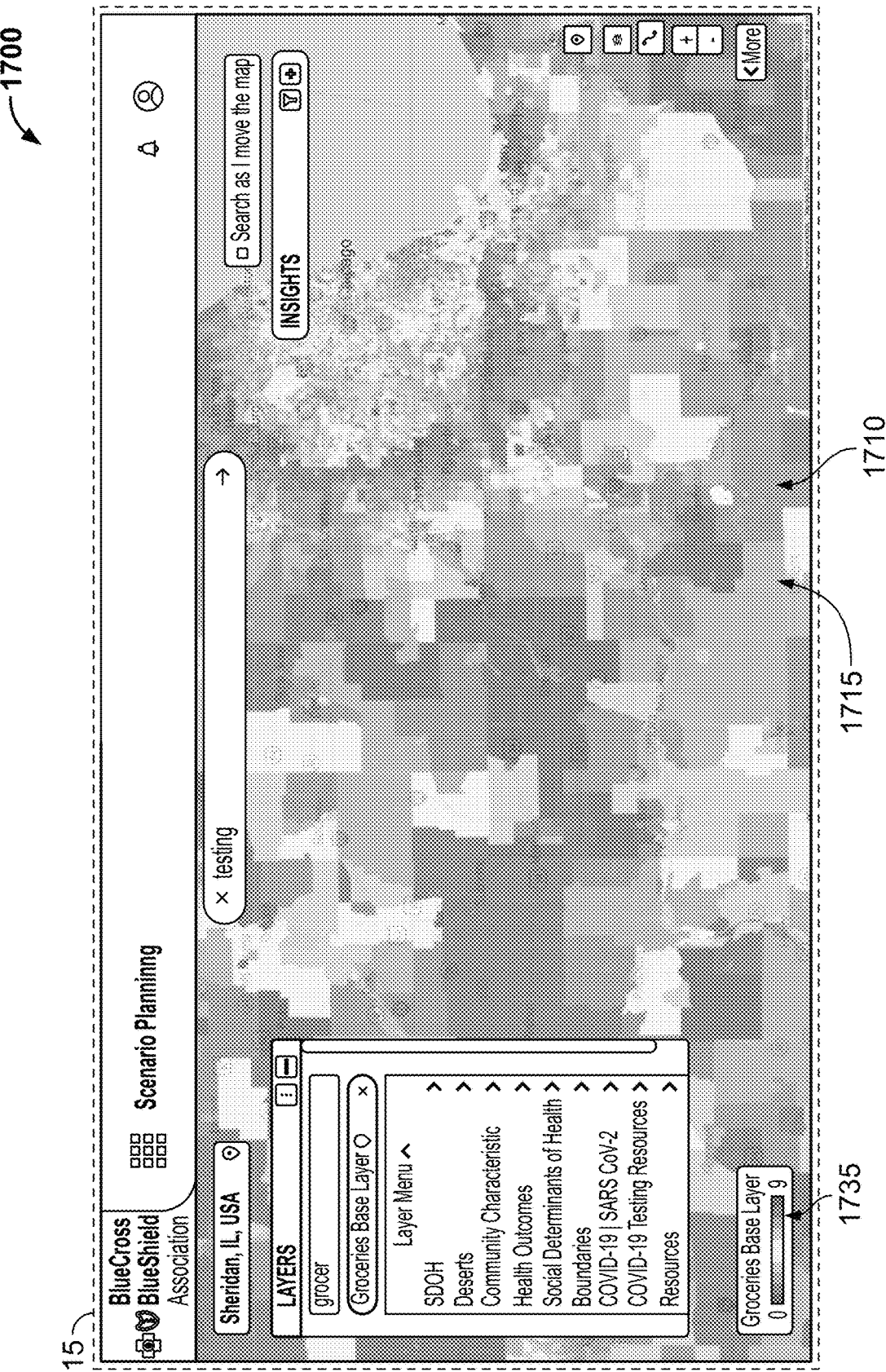
FIG. 17 depicts another example interface for a user of the visualization system of FIG. 1.

FIGS. 17-20 show other example images that are visible to the user on the user's display 15. FIG. 17 shows an interface 1700 that includes a geographic image of the Chicago metropolitan area at a different zoom level chosen by the user. Hundreds of different block groups 1710 overlaid on the map. The different block groups 1710 are illustrated in different geometric shapes as determined by the U.S. Census Bureau. Each of the block groups 1710 are identified with a corresponding score identifier 1715 that represents a desert score of the block group 1710 to the user. Each score identifier 1715 is a different color, shade, or pattern that corresponds to respective ranges of desert scores on a scale. The various score identifiers 1715 are also included on a scale within a legend 1735 to help the user identify the respective range of desert scores of each of the block groups 1710. In this way, a user can quickly identify one or more deserts of a selected resource (e.g., groceries) that currently exist in a selected region (e.g., the Chicago metropolitan area) based on the color or shading of the different block groups 1710.

In various embodiments, the score identifiers 1715 correspond with quantiles such that each score identifier 1715 is associated with a same number of block groups 1710. That is, the block groups 1710 are evenly distributed (e.g., by the Carto Server 400) among the various score identifiers 1715. In FIG. 17, the Carto Server 400 has divided the block groups 1710 into deciles, and each score identifier 1715 corresponds with a different color or shade on a ten-point scale (e.g., represented from 0 to 9 within the legend 1735). For instance, a quantile associated with a score of 0 is represented by dark red shading, a quantile associated with a score of 3 is represented by light red shading, a quantile associated with a score of 6 is represented by light blue shading, and a quantile associated with a score of 0 is represented by dark blue shading. In other embodiments, each of the score identifiers 1715 correspond with a respective group of block groups 1710 that is clustered together using a Jenks algorithm. In some instances, the Carto Server 400 uses a Jenks algorithm to represent prevalence rates within relatively small sample sets (e.g., percentages of Native Americans within a selected region). In other embodiments, each score identifier 1715 correspond with a respective group of block groups 1710 that is determined based on manually-selected cut-off values.

Figure 18:
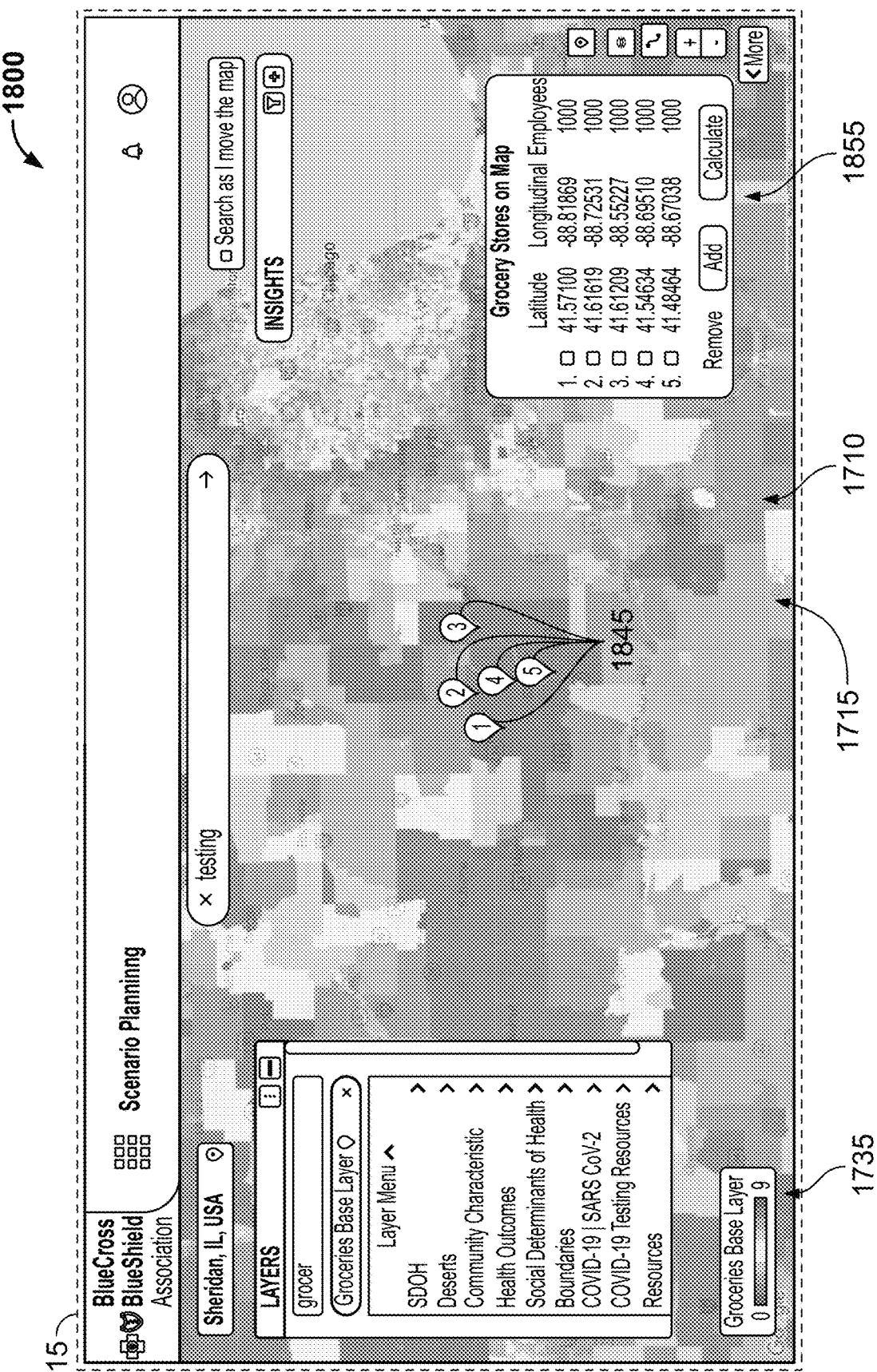
FIG. 18 depicts another example interface for a user of the visualization system of FIG. 1.

FIG. 18 shows another interface 1800 that includes the same image of FIG. 17 after visualization system 100 receives the user's selection of "grocery" type resources among the resource options and the user's placement of one or more new "grocery" type resources 1845 at various locations on the displayed map at a user-selected zoom level with the goal of simulating how the existence and placement of those resources 1845 would affect the desert scores of the block groups 1710. In the illustrated example, five of the resources 1845 are positioned by the user within a subregion of the displayed region. In other examples, the user may place the resources anywhere in the displayed map. A legend 1855 includes tabular data that illustrates the detected latitude and longitude of each of the new resources 1845, as well as the estimated number of employees at each new resource 1845.

Figure 19:
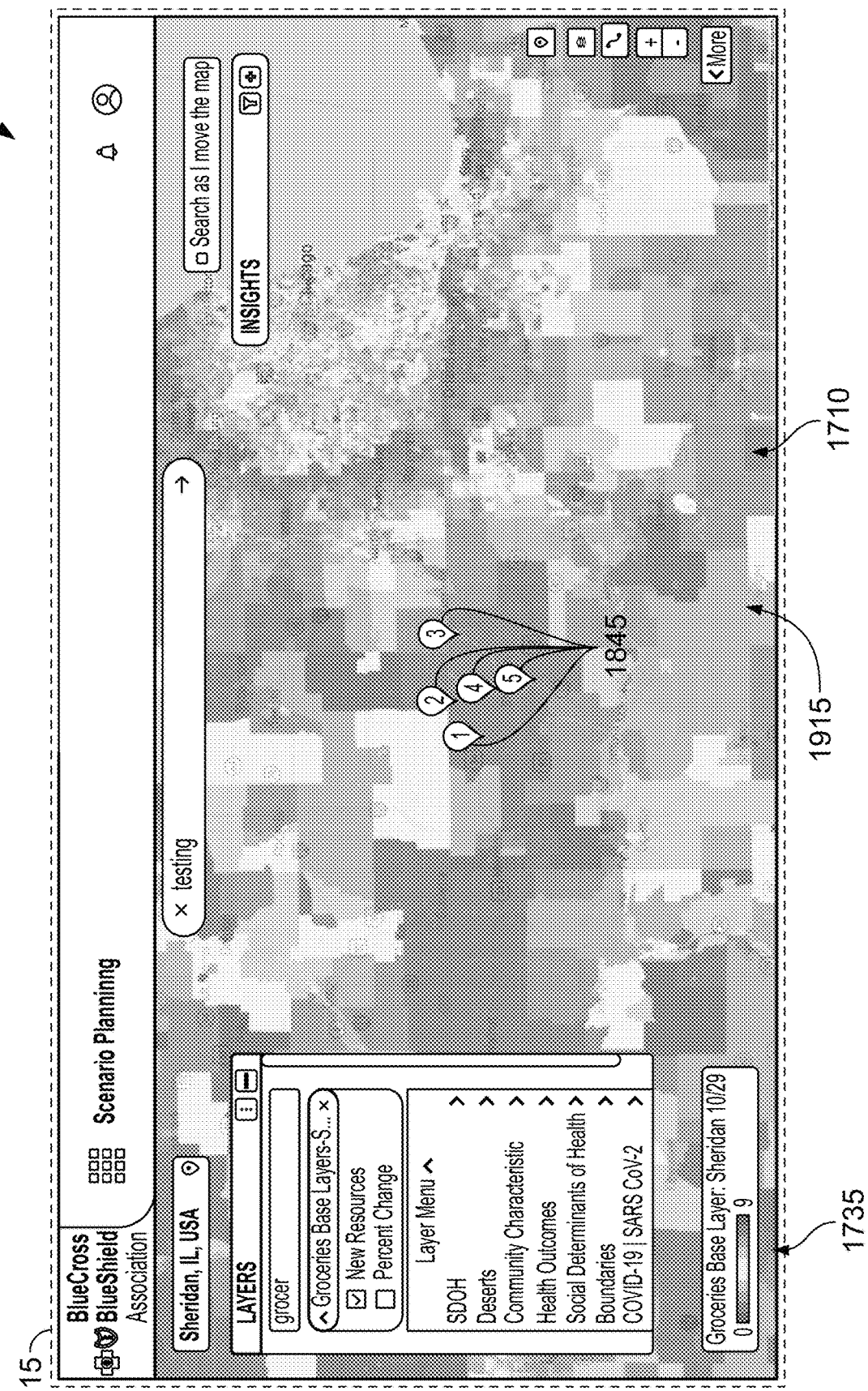
FIG. 19 depicts another example interface for a user of the visualization system of FIG. 1.

FIG. 19 shows another interface 1900 that includes a new set of score identifiers 1915 based on real-time recalculation of new desert scores that take into account the simulated existence and location of the resources 1845 according to the teachings herein. The interface 1900 includes the same geographic image, block groups 1710, and resources 1845 as FIG. 18. For each of the resources 1845 in FIG. 19, the score identifier 1915 has been updated and compared to the respective score identifier 1715 of FIG. 18 to reflect the new desert scores that have been calculated based on the existence, location, and employee count of the resources 1845. In accordance with the teachings herein, the new score identifiers 1915 indicate that block groups 1710 near the resources 1845 have been positively affected by the new resources 1845, while block groups 1710 farther away from the resources 1845 are unaffected by the resources 1845. As shown in FIG. 19, the score identifiers 1915 of the block groups 1710 near the resources 1845 are different than those of the original score identifiers 1715, and the score identifiers 1915 of the block groups 1710 away from the resources 1845 are the same as those of the original score identifiers 1715.

Figure 20:
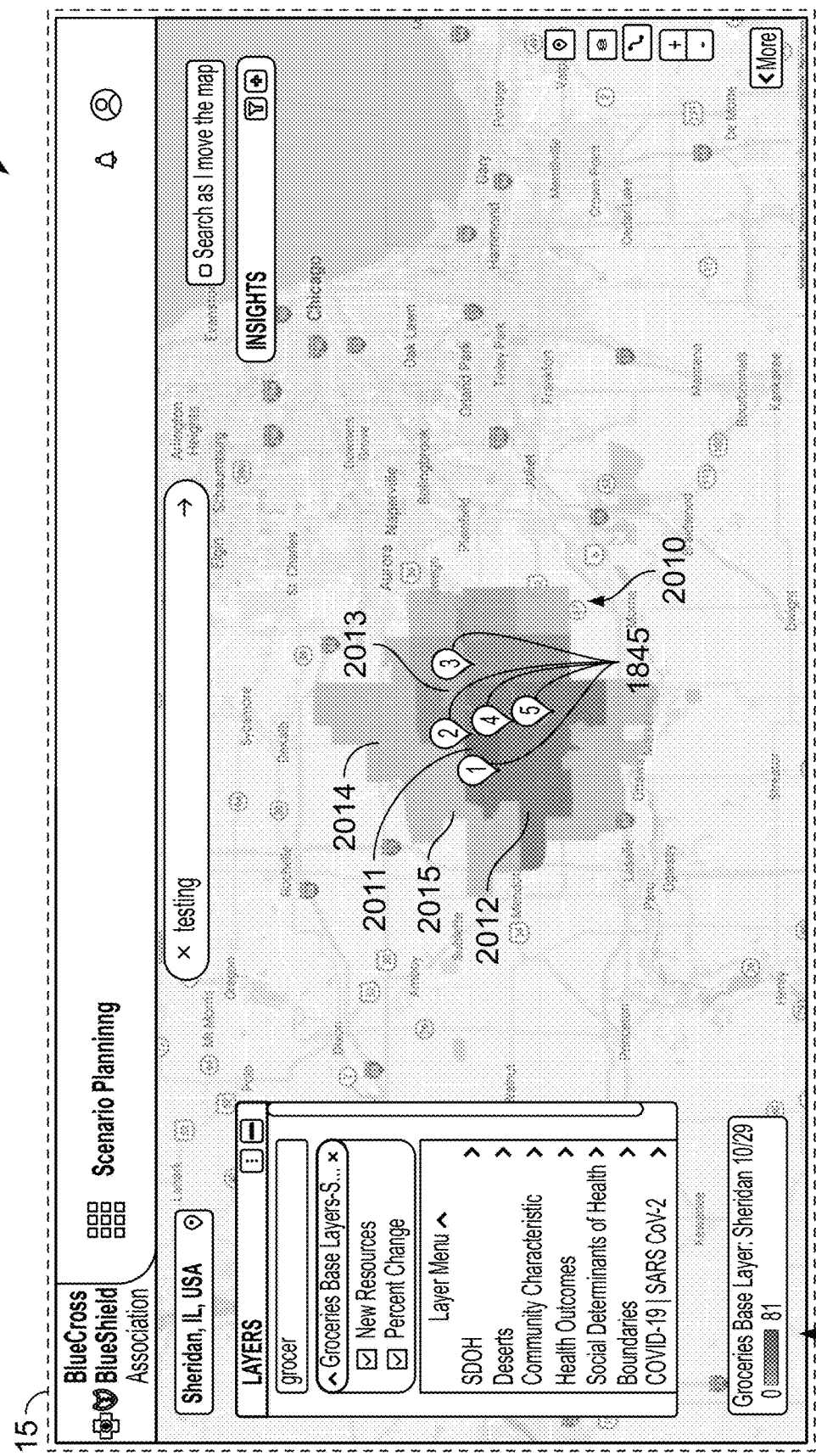
FIG. 20 depicts another example interface for a user of the visualization system of FIG. 1.

FIG. 20 shows another interface 2000 that depicts a comparison between the new score identifiers 1915 of FIG. 19 and the original score identifiers 1715 of FIGS. 17-18. For example, a percent change for a respective block group is calculated using the formula of Percent_Change=(Original_Desert_Score_New_Desert_Score)/Original_Desert_Score. In FIG. 20, only a portion 2010 of block groups 1710 that have been affected by the new resources 1845 are shown. Other block groups 1710 that are too far to have been affected by the new resources 1845 are not shown. Each of the block groups 1710 of the affected portion 2010 are identified with a corresponding percentage identifier that represents a percent change to the user. Each percentage identifier is a different color, shade, or pattern that corresponds to a respective range of percentage changes. The percentage identifiers are also included on a scale within a legend 1735 to facilitate the user in identifying a percentage change of each of the affected block groups. In this way, a user can quickly identify which block groups were most affected by the new resources 1845.

In FIG. 20, there is shown five percentage identifiers 2011, 2012, 2013, 2014, 2015 to represent different ranges of percent change of the portion 2010 of block groups 1710 affected by the resources 1845. Each of the percentage identifiers 2011, 2012, 2013, 2014, 2015 corresponds with a different color or shade represented by a scale (e.g., from a percentage change of 0 to a percentage change of 81) within the legend 1735. For instance, the percentage identifier 2011 is represented by dark green shading to indicate a relatively large percentage change, the percentage 2013 is represented by medium green shading to indicate a relatively average percentage change, and 2015 is represented by light green shading to indicate a relatively small percentage change.

In some embodiments, the percentage identifiers 2011, 2012, 2013, 2014, 2015 separated into quantiles (e.g., quintiles) and/or using a Jenks algorithm. In the illustrated embodiment, the percentage identifiers 2011, 2012, 2013, 2014, 2015 are determined using manually-selected cutoff values of percentage change according to Table 1 provided below:

TABLE 1

| Percentage Identifier | Range | Hex Color |
| --- | --- | --- |
| 2011 | 80% ≤ Δ | #0e5d0e |
| 2012 | 60% ≤ Δ < 80% | #137f13 |
| 2013 | 40% ≤ Δ < 60% | #19a119 |
| 2014 | 2% ≤ Δ < 40% | #1ec31e |
| 2015 | 1% ≤ Δ < 20% | #3be13b |
| n/a | Δ < 1% | Transparent |

In other embodiments, there may be more or fewer ranges of percent change displayed with corresponding colors, shading, or patterns, and the ranges themselves may be smaller or larger in magnitude. For example, Table 2 below shows a different percent change matrix that could be used:

TABLE 2

| Range | Hex Color |
| --- | --- |
| If percent change is ≥100% | Color assigned is #0c4c0c |
| If percent change is 80% ≤ Δ < 100% | Color assigned is #0e5d0e |
| If percent change is 60% ≤ Δ < 80% | Color assigned is #137f13 |
| If percent change is 40% ≤ Δ < 60% | Color assigned is #19a119 |
| If percent change is 20% ≤ Δ < 40% | Color assigned is #1ec31e |
| If percent change is 1% ≤ Δ < 20% | Color assigned is #3be13b |
| If percent change is Δ < 1% | Color assigned is transparent |

One of ordinary skill would appreciate that visualization system 100 may include components and software that can recommend new resources, resource types, and their locations to provide the greatest health and/or financial impact in a designated geographical area. For example, in one embodiment visualization system 100 may be configured to receive or lookup a list of latitudinal and longitudinal coordinates corresponding to two or more proposed new locations for one or more proposed new resources having one or more resource types, and be configured to run an iterative, real-time, simulation that ranks the two or more locations according to their impact on health-related outcomes in the designated geographical area and/or the financial impact of deploying the new resources in the designated geographical area. In this way, a user may easily evaluate the cost v. benefit of the ranked locations of the proposed new resources and resource types. Ranking of resource quantity and resource types may also be performed by visualization system 100 to enable one of ordinary skill to know how many new resources and what type of resources provide the best cost v. benefit to populations in the designated geographical area.

One of ordinary skill would appreciate that the teachings of the instant disclosure can apply to any industry, including any non-health-related resource that requires impact visualization. For example, a corporation with a franchise network may want to know the impact of a new franchise location, including the predicted decrease in consumers and/or consumer traffic at other nearby franchise locations and the predicted consumer traffic at the new franchise location. By using the teachings of the instant disclosure, the corporation can quickly analyze any number of alternate locations for the new franchise without having to wait 2 or more days for nationwide resource data calculations to complete. In addition, the system of the instant disclosure can be configured to allow any number of different user input methods for identifying the location of new resource placement. For example, the system may be configured to receive number or series of hypothetical new resource locations for a given resource type, all of which are arranged in a lookup table. The system can compute the impact of each new resource and store the visualization in memory for recall by the user to toggle through in rapid succession.

Any process descriptions or blocks in the figures, should be understood as representing modules, segments, or portions of code which include one or more executable instructions for implementing specific logical functions or steps in the process, and alternate implementations are included within the scope of the embodiments described herein, in which functions may be executed out of order from that shown or discussed, including substantially concurrently or in reverse order, depending on the functionality involved, as would be understood by those having ordinary skill in the art.

The embodiments described herein are possible examples of implementations and are merely set forth for a clear understanding of the principles of the features described herein. Many variations and modifications may be made to the above-described embodiment(s) without substantially departing from the spirit and principles of the techniques, processes, devices, and systems described herein. All such modifications are intended to be included herein within the scope of this disclosure and protected by the following claims.

What is claimed is:

1. A system for providing an interactive visualization of health resources, the system comprising:
   one or more databases configured to store:
      geographic coordinates of boundaries and center points of block groups, wherein each of the block groups defines a contiguous geographical area in which residents reside;
      geographic coordinates and current crowding levels of pre-existing resources; and
      desert levels of the block groups for resource types, wherein each of the desert levels is indicative of scarcity of a respective one of the resource types in a respective one of the block groups; and
   one or more controllers configured to:
      generate an interface of a geographic region-of-interest for a computing device of a user, the geographic region-of-interest at least partially including one or more of the block groups;
      receive a selected resource type via the computing device of the user;
      for each of the block groups located within the geographic region-of-interest:
         retrieve a respective desert level for the selected resource type; and
         define a sphere of daily economic activity of the block group based on:
            the center of the block group; and
            a radius that extends from the center of the block group and equals an average estimated distance traveled by the residents of the block group;
      receive a user input, via the user device, identifying geographic coordinates of a proposed new resource for the selected resource type within the geographic region-of-interest;
      identify, in real time, one or more affected block groups that are affected by the proposed new resource by determining which of the block groups have a respective sphere of daily economic activity that overlaps with the geographic coordinates of the proposed new resource;
      identify, in real time, one or more affected resources that are affected by the proposed new resource;
      determine, in real time, a new crowding level of each affected resource by dividing a number of people predicted to access the affected resource by a capacity of the affected resource;
      determine, in real time, a new desert score of each affected block group located within the geographic region-of-interest of the interface based on an average of the new crowding levels of the affected resources and the new proposed resource that are within the sphere of daily economic activity of the respective block group; and
      update, in real time, the interface to display the new desert score of each affected block group located within the geographic region-of-interest.

2. The system of claim 1, wherein, for each of the block groups and prior to receipt of the user input, the one or more controllers is configured to:
   identify a geographic population distribution of the residents within the block group;
   determine a population-weighted spatial center of the block group; and
   assign the population-weighted spatial center as the center point of the block group.

3. A method for providing an interactive visualization of health resources, comprising:
   storing, via one or more databases, geographic coordinates of boundaries and center points of block groups, geographic coordinates and current crowding levels of pre-existing resources, and desert levels of the block groups for resource types, wherein each of the block groups is a contiguous geographical area in which residents reside, and wherein each of the desert levels is indicative of scarcity of a respective one of the resource types in a respective one of the block groups;
   generating, via one or more controllers, an interface of a geographic region-of-interest for a computing device of a user, the geographic region-of-interest at least partially including one or more of the block groups;
   receiving a selected resource type via the computing device of the user;
   for each of the block groups located within the geographic region-of-interest: retrieving a respective desert level for the selected resource type; and
      defining a sphere of daily economic activity of the block group based on:
         the center of the block group; and
         a radius that extends from the center of the block group and equals an average estimated distance traveled by the residents of the block group:
   receiving, via the computing device of the user, a user input that identifies geographic coordinates of a proposed new resource for the selected resource type within the geographic region-of-interest;
   identifying, in real time, one or more affected block groups that are affected by the proposed new resource by determining which of the block groups have a respective sphere of daily economic activity that overlaps with the geographic coordinates of the proposed new resource;
   identifying, in real time, one or more affected resources that are affected by the proposed new resource;

determining, in real time, a new crowding level of each affected resource by dividing a number of people predicted to access the affected resource by a capacity of the affected resource;

determining, in real time, a new desert score of each affected block group located within the geographic region-of-interest of the interface based on an average of the new crowding levels of the affected resources and the new proposed resource that are within the sphere of daily economic activity of the respective block group; and updating, in real time, the interface to display the user input and the new desert score of each affected block group located within the geographic region-of-interest.

4. The method of claim 3, further comprising, for each of the block groups and prior to receipt of the user input:

identifying a geographic population distribution of the residents within the block group;

determining a population-weighted spatial center of the block group; and assigning the population-weighted spatial center as the center point of the block group.

5. A computer readable medium comprising instructions, which, when executed by a processor, causes a machine to:

store geographic coordinates of boundaries and center points of block groups, geographic coordinates and current crowding levels of pre-existing resources, and desert levels of the block groups for resource types, wherein each of the block groups is a contiguous geographical area in which residents reside, and wherein each of the desert levels is indicative of scarcity of a respective one of the resource types in a respective one of the block groups;

generate a computer interface of a geographic region-of-interest, the geographic region-of-interest at least partially including one or more of the block groups;

receive a selected resource type;

for each of the block groups located within the geographic region-of-interest:

retrieve a respective desert level for the selected resource type; and define a sphere of daily economic activity of the block group based on:

the center of the block group; and a radius that extends from the center of the block group and equals an average estimated distance traveled by the residents of the block group;

receive a user input that identifies geographic coordinates of a proposed new resource for the selected resource type within the geographic region-of-interest;

identify, in real time, one or more affected block groups that are affected by the proposed new resource by determining which of the block groups have a respective sphere of daily economic activity that overlaps with the geographic coordinates of the proposed new resource;

identify in real time, one or more affected resources that are affected by the proposed new resource;

determine, in real time, a new crowding level of each affected resource by dividing a number of people predicted to access the affected resource by a capacity of the affected resource;

determine, in real time, a new desert score of each affected block group located within the geographic region-of-interest of the computer interface based on an average of the new crowding levels of the affected resources and the new proposed resource that are within the sphere of daily economic activity of the respective block group; and update, in real time, the computer interface to display the user input and the new desert score of each affected block group located within the geographic region-of-interest.

6. The computer readable medium of claim 5, wherein, for each of the block groups and prior to receipt of the user input, the instructions, when executed by the processor, further cause the machine to:

identify a geographic population distribution of the residents within the block group;

determine a population-weighted spatial center of the block group; and assign the population-weighted spatial center as the center point of the block group.

7. The system of claim 1, wherein the one or more controllers is configured to determine the average estimated distance traveled by the residents for each of the block groups based on survey data.

8. The system of claim 1, wherein the one or more controllers is configured to identify each of the one or more affected block groups via a point-set intersection routine, and wherein each of the one or more affected block groups identified by the one or more controllers is:

a primary block group whose respective sphere of daily economic activity encompasses the proposed new resource; or a secondary block group that shares at least one of the pre-existing resources with at least one primary block group.

9. The system of claim 1, wherein the one or more affected resources includes each of the pre-existing resources that is in the respective sphere of daily economic activity of at least one of the one or more affected block groups.

10. The system of claim 1, wherein, to determine the respective number of people predicted to access each of the one or more affected resources, the one or more controllers is configured to:

determine a respective resident count predicted to access the affected resource for each of the one or more affected block groups; and sum the resident counts together.

11. The system of claim 10, wherein, to determine the respective resident count for each of the one or more affected block groups, the one or more controllers is configured to:

identify a distance between the proposed new resource and the center point of the respective affected block group; and apply a cubic delay function to the distance between the proposed new resource and the center point of the respective affected block group.

12. The system of claim 1, wherein, for each of the one or more affected resources, one or more controllers is configured to assign a number of employees of the affected resource as the capacity of the affected resource.

13. The method of claim 3, wherein the one or more affected block groups are identified via a point-set intersection routine, and wherein each of the one or more affected block groups is:

a primary block group whose respective sphere of daily economic activity encompasses the proposed new resource; or a secondary block group that shares at least one of the pre-existing resources with at least one primary block group.

14. The method of claim 3, wherein the one or more affected resources includes each of the pre-existing resources that is in the respective sphere of daily economic activity of at least one of the one or more affected block groups.

15. The method of claim 3, further comprising determining the respective number of people predicted to access each of the one or more affected resources by:
   determining a respective resident count predicted to access the affected resource for each of the one or more affected block groups; and
   summing the resident counts together.

16. The method of claim 15, wherein determining the respective resident count for each of the one or more affected block groups comprises:
   identifying a distance between the proposed new resource and the center point of the respective affected block group; and
   applying a cubic delay function to the distance between the proposed new resource and the center point of the respective affected block group.

17. The computer readable medium of claim 5, wherein the one or more affected block groups are identified via a point-set intersection routine, and wherein each of the one or more affected block groups is:
   a primary block group whose respective sphere of daily economic activity encompasses the proposed new resource; or
   a secondary block group that shares at least one of the pre-existing resources with at least one primary block group.

18. The computer readable medium of claim 5, wherein the one or more affected resources includes each of the pre-existing resources that is in the respective sphere of daily economic activity of at least one of the one or more affected block groups.

19. The computer readable medium of claim 5, wherein, to determine the respective number of people predicted to access each of the one or more affected resources, the instructions, when executed, further cause the machine to:
   determine a respective resident count predicted to access the affected resource for each of the one or more affected block groups; and
   sum the resident counts together.

20. The computer readable medium of claim 5, wherein, to determine the respective resident count for each of the one or more affected block groups, the instructions, when executed, further cause the machine to:
   identify a distance between the proposed new resource and the center point of the respective affected block group; and
   apply a cubic delay function to the distance between the proposed new resource and the center point of the respective affected block group.

* * * * *